US007202044B2

(12) United States Patent
Lamping et al.

(10) Patent No.: US 7,202,044 B2
(45) Date of Patent: Apr. 10, 2007

(54) METHOD FOR DETECTING A PROGRESSIVE, CHRONIC DEMENTIA DISEASE, AND CORRESPONDING PEPTIDES AND DETECTION AGENTS

(75) Inventors: Norbert Lamping, Hannover (DE); Hans-Dieter Zucht, Hannover (DE); Harmut Selle, Hannover (DE); Michael Jürgens, Hannover (DE); Gabriele Heine, Hannover (DE); Rüdiger Hess, Hannover (DE)

(73) Assignee: Biovision AG (DE)

( * ) Notice: Subject to any disclaimer, the term of this patent is extended or adjusted under 35 U.S.C. 154(b) by 244 days.

(21) Appl. No.: 10/476,976

(22) PCT Filed: May 8, 2002

(86) PCT No.: PCT/DE02/01665

§ 371 (c)(1),
(2), (4) Date: Nov. 7, 2003

(87) PCT Pub. No.: WO02/090974

PCT Pub. Date: Nov. 14, 2002

(65) Prior Publication Data
US 2004/0152138 A1 Aug. 5, 2004

(30) Foreign Application Priority Data
May 9, 2001 (DE) .............................. 101 22 543

(51) Int. Cl.
*G01N 33/53* (2006.01)
*G01N 33/567* (2006.01)
*G01N 33/536* (2006.01)
*A61K 38/28* (2006.01)
*C07K 5/00* (2006.01)
*C07K 14/00* (2006.01)

(52) U.S. Cl. ..................... 435/7.21; 436/516; 436/451; 436/536; 530/305

(58) Field of Classification Search ...................... None
See application file for complete search history.

(56) References Cited

FOREIGN PATENT DOCUMENTS

| WO | WO98/08379 | 8/1996 |
|---|---|---|
| WO | WO00/63241 | 4/1999 |
| WO | WO01/71358 | 3/2001 |
| WO | WO01/75165 | 3/2001 |
| WO | WO02/081522 | 4/2002 |
| WO | WO02/092122 | 5/2002 |

OTHER PUBLICATIONS

Butler W. T. Connect Tissue Res. 1989;23(2-3):123-36.*
Stark et al. J. Chromat. B. 2001: 357-367.*
Keifer, et al.; The CDNA and derived amino acid sequences for human osteopontin Nucleic Acids Research, Oxford University Press; ?Surrey GB; vol. 17 No. 8, 1989 p. 3306.
Oral Health Sciences Unit Projects; School of Dental Science; Faculty of Science, Faculty of Medicine, Dentistry and Health Sciences; Sep. 2000; L. Huq, et al. The University of Melbourne.

* cited by examiner

*Primary Examiner*—Janet L. Andres
*Assistant Examiner*—Chang-Yu Wang
(74) *Attorney, Agent, or Firm*—Sills Cummis Epstein & Gross

(57) ABSTRACT

The invention relates to defined peptides and the quantitative determination thereof in body fluids of patients suffering from progredient chronic dementia, in relation to the concentration of said peptides in a control group. The inventive peptides come from a protein precursor having the corresponding gene, are processed in a specific manner, and are optionally post-translationally modified, especially phosphorylized. An increase in the concentrations of these peptides or the corresponding non-processed protein indicates progredient chronic dementia. Progredient chronic dementia is detected by identifying the peptides and/or the protein individually or in combinations. The invention also relates to the use of said peptides for controlling the course of progredient chronic dementia and for the prognosis of progredient chronic dementia, especially for complementing or replacing mini-mental scores, and for developing therapeutic agents to combat progredient chronic dementia such as Alzheimer's disease.

10 Claims, 10 Drawing Sheets

Figure 2:
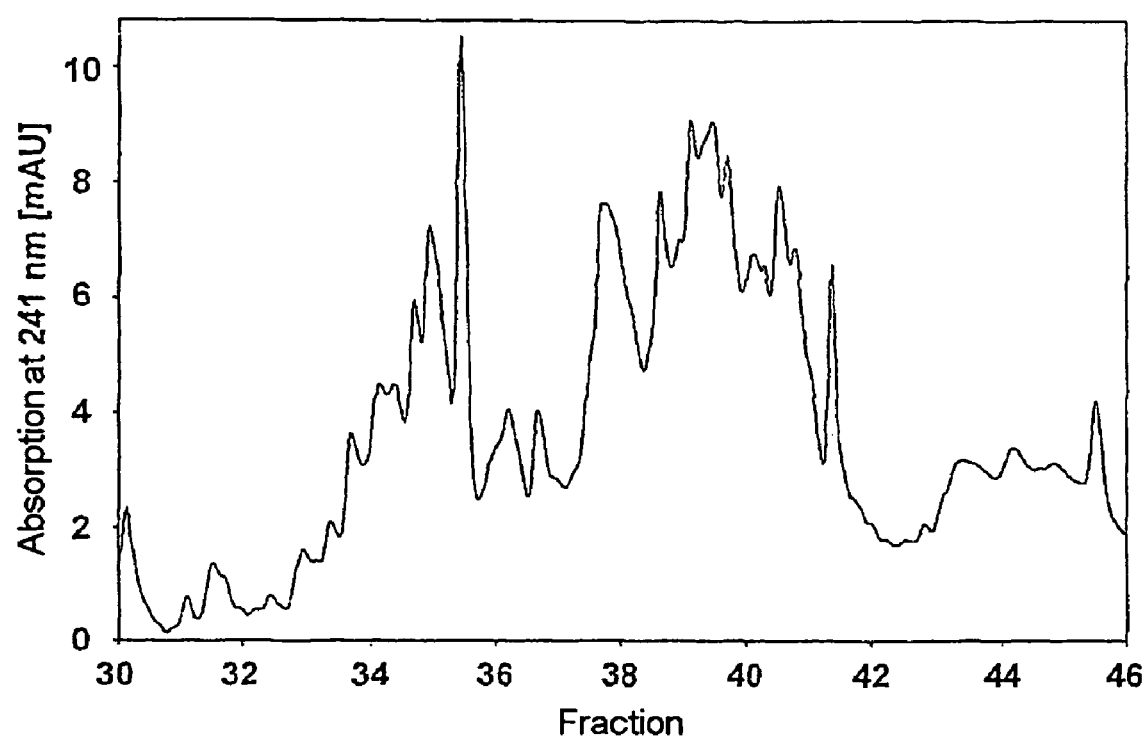

| OPN protein | 1 MRIAVICFCLLGITCAIPVKQADSGSSEEKQLYNKYPDAVATWLNP |
|---|---|
| DROPN-1 | ..........................VKQADSGSSEEKQLYNKYPDAVAT..... |
| DROPN-27 | ..........................VKQADSGSSEEKQLYNKYPDAVA...... |
| DROPN-28 | ...........................KQADSGSSEEKQLYNKYPDAVAT..... |
| DROPN-2 | .................................r1-SEEKQLYN-r2......... |

| OPN protein | 47 DPSQKQNLLAPQNAVSSEETNDFKQETLPSKSNESHDHMDMDDEDDDHVDSQDSIDSNDSDDVDD |

| OPN protein | 114 TDDSHQSDESHHSDESDELVTDFPTDLPATEVFTPVVPTVDTYDGRGDSVVYGLRSKSKKFRRPDIQ |

| OPN protein | 181 YPDATDEDITSHMESEELNGAYKAIPVAQDLNAPSDWDSRGKDSYETSQLDDQSAETHSHKQSRLYK |
|---|---|
| DROPN-3 | .......................AQDLNAPSDWDSRGKDSYETSQLDDQSAETHSHKQS..... |
| DROPN-4 | .......................AQDLNAPSDWDSRGKDSYETSQLDDQSAETHSHKQSRLY. |
| DROPN-29 | ........................QDLNAPSDWDSRGKDSYETSQLDDQSAETHSHKQSRLY. |
| DROPN-5 | ........................QDLNAPSDWDSRGKDSYETSQLDDQSAETHSHKQS..... |
| DROPN-6 | ...........................LNAPSDWDSRGKDSYETSQLDDQSAETHSHKQS..... |
| DROPN-7 | .....................................................DDQSAETHSHKQSRL. |
| DROPN-8 | .....................................................DDQSAETHSHKQSRLY. |
| DROPN-9 | ...........................................r3-KDSYETSQ-r4......... |
|  | ...........................................................r5-SAETHSHK-r6... |

Figure 1A:

```
OPN protein   248 RKANDESNEHSDVIDSQELSKVSREFHSHEFHSHEDMLVVDPKSKEEDKHLKFRISHELDSASSEVN DROPN-10          .KANDESNEHSDVIDSQELSKVSREFHSHEFHSHEDMLVVDPKSKEEDKHLKFRISHELDSASSEVN
DROPN-11          .KANDESNEHSDVIDSQELSKVSREFHSHEFHSHEDMLVVD..........................
DROPN-30          ...NDESNEHSDVIDSQELSKVSREFHSHEFHSHEDML.............................
DROPN-31          ...NDESNEHSDVIDSQELSKVSREFHSHEFHSHEDM..............................
DROPN-12          ...................SKVSREFHSHEFHSHED...............................
DROPN-13          ...r7-SNEHSDVI-r8..................................................
DROPN-14          ....................r9-REFHSHEF-r10................................
DROPN-15          .....................................LVVDPKSKEEDKH.................
DROPN-16          .....................................LVVDPKSKEEDKHL................
DROPN-17          .....................................LVVDPKSKEEDKHLK...............
DROPN-18          .....................................LVVDPKSKEEDKHLKF..............
DROPN-19          .....................................LVVDPKSKEEDKHLKFRISHELDSASSE..
DROPN-20          .....................................LVVDPKSKEEDKHLKFRISHELDSASSEVN
DROPN-21          ......................................VVDPKSKEEDKHLK...............
DROPN-22          ......................................VVDPKSKEEDKHLKF..............
DROPN-23          ......................................VVDPKSKEEDKHLKFRISHELDSASSE..
DROPN-24          .........................................PKSKEEDKHLKFRISHELDSASSE..
DROPN-25          ......................................r11-KSKEEDKH-r12.............
DROPN-26          ....................................................r13-SHELDSAS-r14
```

METHOD FOR DETECTING A PROGRESSIVE, CHRONIC DEMENTIA DISEASE, AND CORRESPONDING PEPTIDES AND DETECTION AGENTS

The invention relates to a method for detecting progressive, chronic dementia diseases or a predisposition to such diseases, in particular an alternative or supplementary method to the determination of the mini-mental score by determining the severity of the dementia. For this purpose, the concentration of particular peptides and body fluids or other samples from the patient is determined. The invention further relates to peptides which have been found for determining the presence and/or the degree of the progressive, chronic dementia disease.

The invention additionally relates to detection reagents such as antibodies and nucleic acids and the like, via which these peptides or the corresponding nucleic acids can be detected. The invention further relates to pharmaceutical applications which comprise OPN, OPN peptides, OPN antibodies, OPN nucleic acids, OPN protein antagonists, or OPN protein agonists, OPN peptide agonists or OPN peptide antagonists, for the therapy or prophylaxis of neurological diseases, especially of Alzheimer's disease. The invention further relates to methods for identifying patients with neurological diseases, especially Alzheimer's disease, who are suitable for taking part in clinical studies to investigate these diseases.

Dementia diseases represent an increasing problem in industrialized countries because of the higher average life expectancy. Dementia diseases are in most cases incurable and make long-term care of the patients necessary. About half of these patients receive inpatient care. More than 60 dementia diseases are known, including diseases associated with manifestations of dementia.

However, Alzheimer's disease (AD) accounts for about 65% of these, and the diagnosis and therapy thereof is therefore of great importance. Besides Alzheimer's disease, the following non-Alzheimer's dementias are known, inter alia: vascular dementia, Lewy body dementia, Binswanger dementia, and dementia diseases which occur as concomitant effect of other disorders such as Parkinson's disease, Huntington's disease, Pick's disease, Gerstmann-Straussler-Scheinger disease, Kreuzfeldt-Jakob disease etc.

Alzheimer's disease is a neurodegenerative disease distinguished by the following symptoms: decline in intellectual abilities, confusion and diminished ability to look after themselves. A greatly restricted short-term memory in particular is characteristic of Alzheimer's disease, whereas the patient's memories of the distant past, e.g. of his/her own childhood, is impaired far less by the disease. There are morphological changes in the brain manifested inter alia in the form of amyloid deposits and degenerated nerve cells. The morphological changes can be diagnosed histologically after the patient's death and are as yet the only reliable detection of the disease. These histopathological diagnoses are based on criteria fixed by the Consortium to Establish a Registry for Alzheimer's Disease (CERAD). The following criteria-based diagnostic systems are currently used to diagnose Alzheimer's disease: the International Classification of Diseases, 10th revision (ICD-10), the Diagnostic and Statistical Manual of Mental Disorders, 4th edition (DSM-IV) of the American Psychiatric Association, and the Work Group crieria drawn up by the National Institute of Neurological and Communicative Disorders Association NINCDS-ADRDA.

These systems use a number of neuropsychological tests in order to diagnose Alzheimer's disease, but not objectively measurable clinical parameters. It is of particular interest to establish the current degree of severity of the disease, which can take place for example by determining the mini-mental score. The mini-mental score is determined with the aid of a mini-mental state examination (MMSE), a psychological test. This makes it possible inter alia to observe the course of the disease and the efficacy of any therapies. However, Clark et al were able to show that, for example, determination of the mini-mental score has only limited validity for determining the course of Alzheimer's disease because large measurement inaccuracies and wide variations in the level of the score occur [1]. The provision of a reliable, clinically measurable parameter which can supplement or replace the mini-mental score for determination of the course of progressive, chronic dementia diseases such as, for example, Alzheimer's disease is therefore of great medical, and thus also economic, importance.

At present, no causal therapy is available for the treatment of Alzheimer's disease. The disease is merely treated symptomatically, e.g. by administration of neurotransmitters such as acetylcholine. Further possible therapeutic strategies being tested at present are the administration of antioxidants, of radical scavengers, of calcium channel blockers, of anti-inflammatory substances, of secretase inhibitors, of anti-amyloid antibodies etc., and immunization against amyloid peptides. However, no causal therapy of this disease is yet possible.

The invention is based on the object of avoiding the prior art disadvantages in the diagnosis of Alzheimer's disease and of providing a method which can be used early and reliably for detecting chronic dementia diseases, especially Alzheimer's disease.

Novel therapies for the treatment of Alzheimer's disease are made possible for the first time by this diagnosis.

Definitions:

OPN proteins or peptides corresponding to accession No. X13694 (SEQ ID NO: 32): The peptide derived from the nucleic acid sequence X13694 (SEQ ID NO: 32) is also referred to as OPN protein and includes all naturally occurring alleles, mutants and polymorphisms of OPN proteins, and tissue-specifically expressed OPN variants. Included in particular are also the OPN variants which occur because of diseases or as a result of neurological diseases, especially chronic dementia diseases, especially Alzheimer's disease. There is inclusion both of OPN proteins with and without signal sequence, proforms of OPN proteins which have not yet been processed, and already processed OPN proteins, soluble OPN proteins and membrane-associated OPN proteins, where the membrane-associated OPN proteins may be linked both via transmembrane amino acid sequences to a cell membrane or organelle membrane nd via a post-translational modification, e.g. a glycosyl-phosphatidyl-inositol (GPI) anchor. Also included are variations of the OPN sequence which [lacuna] by alternative splicing, by alternative translation starting and termination points, by RNA editing, by alternative post-translational modifications, and other OPN protein variants arising through naturally occurring mechanisms.

DROPN peptides:

OPN peptides and OPN peptide variants are referred to hereinafter as DROPN ("dementia related osteopontin") peptides. DROPN peptides are derived from the OPN sequence X13694 (SEQ ID NO: 32) mentioned at the outset. Alternatively, DROPN peptides may also be derived from other Gene Bank entries for osteopontin, such as, for example, AF052124, J04765, M83248, $NM_{13}$ 000583, U20758 or further OPN entries which will possibly also be added in future. It is moreover possible for the OPN protein sequences possibly to differ from the sequence of the Gene Bank entry with the number X13694 (SEQ ID NO: 32), as is currently the case already for the Gene Bank entries AF052124, J04765 and NM_000582. OPN sequence entries may also be present in other sequence databases different from "Gene Bank". Consequently, DROPN peptides and OPN proteins need not agree exactly with the sequence of the OPN protein corresponding to the entry in the "Gene Bank" sequence database with the accession No. X13694 (SEQ ID NO: 32). In addition, DROPN peptides may include two point-mutated, two deleted or two additionally internally inserted amino acids, and N-terminal andior C-terminal extensions. However, in these cases they must retain at least 8 amino acids from the OPN protein sequence. The only amino acids suitable as N- or C-terminal extensions are those occurring in the OPN protein sequence at this sequence position in the OPN protein. Peptides derived from naturally occurring OPN polymorphisms and from naturally occurring OPN mutants are also referred to as DROPN peptides as long as they show at least 70% agreement with the OPN protein sequence (X13694, SEQ ID NO: 32). DROPN peptides may also exist with post-translational modifications such as, for example, phosphorylations or N-terminal pryroglutamic acid residues and/or in chemically modified form, preferablyas peptide oxides. For example, DROPN-10 (SEQ ID NO: 10) has been identified both as non-phosphorylated and as phosphorylated peptide. DROPN-10 (SEQ ID NO: 10) occurs, for example, without phosphate group and with one, two, three, four or five phosphate groups.

Chemically or Post-Translationally Modified Peptides:

A chemically or post-translationally modified peptide may consist both of D- and of L-amino acids, and of combinations of D- and L-amino acids and may occur naturally, be prepared recombinantly or synthesized chemically. These peptides may additionally comprise unusual amino acids, i.e. amino acids which do not belong to the 20 standard amino acids. Examples of unusual amino acids are, inter alia: alpha-aminobutyric acid, beta-aminobutyric acid, beta-alanine, beta-aminoisobutyric acid, norvaline, homoserine, norleucine, gamma-aminobutyric acid, thioproline, 4-hydroxyproline, alpha-aminoadipic acid, diaminobutyric acid, 4-aminobenzoic acid, homocysteine, alpha-aminopenicillanic acid, histamine, ornithine, glycineproline dipeptide, hydroxylysine, proline-hydorxyproline dipeptide, cystathionine, ethionine, seleno-cysteine. Possible post-translational or chemical modifications are, inter alia, modifications of amino acid sequences by the following structures: linkage of free cysteine to a cysteine in the peptide sequence, methyl, acetyl, farnesyl, biotinyl, stearoyl, palmityl, lipoyl, C-mannosyl, phosphorus and sulfate groups, glycosilations, amidations, deamidations, pyroglutamic acid, citrulline etc.

Nucleic Acids:

Nucleic acids are regarded as being DNA, RNA and DNA-RNA hybrid molecules both of natural origin and prepared synthetically or by recombination. Also included are chemically modified nucleic acids which comprise modified nucleotides having high in vivo stability, such as, for example, phosphorothioates. Such stabilized nucleic acids are already used in the application of ribozyme, antisense and triplex nucleic acid techniques.

Significance:

The term significant is used in the sense in which the term significance is used in statistics. In this patent application, an error probability of less than 90%, preferably 95% further preferably 99% is defined as significant.

Sensitivity:

Sensitivity is defined as the proportion of patients with the disease who acquire a positive diagnostic result in a diagnosis for the disease, i.e. the diagnosis correctly indicates the disease.

Specificity:

The specificity is defined as the proportion of healthy patients who acquire a negative diagnostic result in a diagnosis for the disease, i.e. the diagnosis correctly indicates that no disease is present.

It has surprisingly been found that in samples of body fluids from patients suffering from Alzheimer's disease, especially in the cerebrospinal fluid, the concentration of certain peptides is changed greatly relative to their concentration in control samples, and thus makes detection of Alzheimer's disease possible. Changes in the concentration of these peptides relative to their concentration in control groups indicate the presence of Alzheimer's disease and are therefore suitable for detecting this disease with high sensitivity and specificity. Modulation of the OPN protein or DROPN peptide concentration with the aim of adjusting the patient to normal OPN or DROPN peptide concentrations can thus be used therapeutically.

To achieve the object, the invention includes a method for detecting a neurological, in particular of a chronic dementia disease, in particular of Alzheimer's disease, or of a predisposition to such a disease by identifying one or more DROPN peptides or OPN peptides which are derived from the sequence having the Gene Bank accession No. X13694 (SEQ ID NO: 32) in a biological sample from an individual. Since these DROPN peptides or OPN peptides are presumably causally connected with the disease, the present invention also includes the use of these peptides for the therapy of Alzheimer's disease or related neurological diseases.

To achieve the object, the invention indicates a method for detecting a neurological disease, in particular a progressive, chronically dementia disease, in particular Alzheimer's disease, by determination of at least one marker peptide in a biological sample from a patient.

Various approaches to achieving this are possible and customary in medical diagnosis:

On the one hand, it is possible generally to investigate for the presence of a marker peptide, and the absence or presence of this marker peptide then makes it possible to diagnose the disease.

In another customary diagnostic strategy, firstly the concentrations of the marker peptide which are normally present in controls and in patients suffering from the disease to be diagnosed are determined and, on the basis of these measurements, a limiting value, frequently also called a cut-off point, which separates the group regarded as healthy from the group regarded as ill is determined. If the concentration of the particular marker peptide is reduced in people with the disease, all those whose measurement for the particular marker peptide is below the cut-off point are diagnosed as having the disease. If the concentration of the particular marker peptide is increased in people with the disease, all those whose measurement for the particular marker peptide is above the cut-off point are diagnosed as having the disease. The cut-off point determined individually for each marker peptide thus makes it possible to distinguish healthy people and people with the disease unambiguously.

In a further diagnostic strategy, an increase in the concentration or reduction in the concentration, which is specific for the particular marker peptide, of the marker peptide in the patient's sample relative to the concentration of the marker peptide in the control sample is determined and a significant marker peptide concentration change is regarded as positive detection result for the disease. In this connection, either in principle only an increase in the peptide concentration of a particular DROPN peptide may occur in patients with Alzheimer's disease, or in principle only a reduction in the peptide concentration of this DROPN peptide may occur in patients with Alzheimer's disease. For a defined DROPN peptide it is not possible at the same time for an increased DROPN peptide concentration to occur in an individual patient with Alzheimer's disease and for a DROPN peptide concentration which is reduced relative to the control group to occur in another patient with Alzheimer's disease.

Preferred markers according to the invention are indicated in the sequence listing and are named from DROPN-1 to DROPN-31, corresponding to Seq. ID 1 to 31. The sequences of the DROPN peptides are depicted in FIG. 1 and in Table 1. The assignment of the DROPN peptides to their respective Seq. ID No. is shown in Table 1.

The method of the invention comprises a method in which there is measurement of specific biomarkers whose concentration is changed in neurodegenerative diseases, especially in Alzheimer's disease, and which indicate the disease even in a very early stage, e.g. when a minimal cognitive impairment (MCI) is present, or indicate an increased risk of the disease at an early date. This is important in order to provide a reliable clinical marker for diagnosing these diseases.

It is possible and preferable for the concentration of DROPN peptides in the sample, but also the characteristic pattern of occurrence of the plurality of particular DROPN peptides, to be correlated with the severity of the disorder. These novel markers therefore make it possible to develop and monitor therapies for the treatment of Alzheimer's disease, because the course and any successful cure resulting from a therapy or a diminished progression of the disease can be established. Effective therapy of Alzheimer's disease is not possible at present, underlining the urgency for the provision of a reliable detection method for Alzheimer's disease, because reliable detection of the disease is a precondition for the development of a therapy.

Detection of DROPN peptides additionally makes it possible in the framework of clinical studies to develop novel therapies for the treatment of Alzheimer's disease with high specificity to select only those patients suffering from Alzheimer's disease and not from other diseases. This is important for obtaining valid study results. Patients incorrectly diagnosed as Alzheimer's disease patients have a negative influence on the quality of the results of a study on Alzheimer's disease therapy. In addition, detection of DROPN peptides makes it possible to stratify patients, enabling the specific selection of subgroups of Alzheimer's disease patients who are especially suitable for particular Alzheimer's disease therapeutic strategies or clinical studies.

There are marked changes in the concentrations of DROPN peptides in Alzheimer's disease patients relative to healthy people. A further aspect of the invention is therefore a bringing of the DROPN concentrations in Alzheimer's disease patients to normal concentrations. This method can be employed for the therapy of Alzheimer's disease or related neurological diseases. If the OPN protein or DROPN peptide concentrations are elevated, the concentrations of these substances can be reduced by therapeutic administration of, for example, OPN protein- or DROPN peptide-specific antibodies or OPN-specific antisense nucleic acids, ribozymes or triplex nucleic acids for DROPN peptide antagonists, OPN protein antagonists. Substances which suppress the endogenous expression of OPN protein or the processing of OPN protein to DROPN peptides can also be administered for the therapy. If the disease is caused by a deficiency of OPN protein or DROPN peptides, therapeutic doses of OPN protein, DROPN peptides, DROPN peptide agonists or OPN protein agonists can be given. Substances which influence the processing of OPN protein to DROPN peptides can also be employed therapeutically. As can be seen in FIG. 1, for example, DROPN-4 (SEQ ID NO: 4) and DROPN-10 (SEQ ID NO: 10) are separated from one another by two basic amino acids (lysine and arginine), and such so-called "dibasic sequences" are often the points of attack of proteases which are involved in the processing of proteins to biologically active peptides. Combination of different therapeutic strategies is, of course, also possible and sensible in some circumstances.

The invention therefore also encompasses the use of OPN proteins, DROPN peptides, DROPN peptide agonists and DROPN antagonists, OPN protein agonists and OPN protein antagonists, anti-OPN protein antibodies and anti-DROPN peptide antibodies for the direct or indirect modulation of the concentration of the OPN proteins and DROPN peptides for the treatment of neurological diseases, especially Alzheimer's disease. Alternative to antibodies, it is also possible to use antibody fragments, antibody fusion proteins, or other substances which bind selectively to OPN proteins or DROPN peptides. It is also possible as alternative to said proteins and peptides for fusion proteins of said proteins and peptides to be used. The invention further encompasses also the use of antisense nucleic acids, triplex nucleic acids and ribozymes which modulate the expression of said proteins and peptides. The invention additionally encompasses agonists and antagonists which modulate the activity of said proteins.

A further embodiment of the invention is the pharmaceutical formulation or chemical modification of the described peptides and nucleic acids to make it possible for them to cross the blood-brain barrier and/or the blood-CSF barrier more efficiently. They are thus made particularly suitable for therapeutic use. In order to achieve this, it is possible for example for DROPN peptides, OPN proteins, nucleic acids, agonists or antagonists to be modified so that for example they become more lipophilic, favoring entry into the subarachnoid space. This can be achieved by introducing hydrophobic molecular constituents or else by "packaging" the substances in hydrophobic agents, e.g. liposomes. It is additionally possible for example for peptide sequences to be attached to these peptides, proteins, nucleic acids, agonists or antagonists, which favor entry into the subarachnoid space or, conversely, impede emergence from the subarachnoid space.

The invention also encompasses the administration of said therapeutic agents by various routes such as, for example, as intravenous injection, as substance which can be administered orally, as inhalable gas or aerosol, or administration in the form of direct injection into the subarachnoid space, or into tissue such as muscle, fat, brain etc. It is possible in this way to achieve increased bioavailability and efficacy of these therapeutic agents. For example, peptides or proteins administered orally can be protected by acid-resistant capsules from proteolytic degradation in the stomach. Very hydrophobic substances can become more hydrophilic and thus better suited for, for example, intravenous injections by suitable pharmaceutical processing etc.

A further embodiment of the invention is the use of DROPN peptides or of OPN proteins for identifying receptors which selectively bind these molecules. These receptors can also be modulated by administration of agonists or antagonists, which is expedient for the therapy of neurological diseases, especially of Alzheimer's disease.

OPN Biology

OPN is synthesized by osteoclasts and osteocytes [2] and incorporated into bone. Osteopontin has been detected immunohistologically in the mineralizing zone of developing bones [3]. It is additionally present in various biological fluids such as, for example, urine and milk, and is expressed by activated T cells [4, 5] and by metastasizing tumor cells, elastic fibers of the skin and of the aorta, myocytes, endothelial cells, macrophages and glia cells [6]. Detection of OPN in the cerebrospinal fluid has not previously been described and the knowledge about the concentration and the presence of OPN in the CSF is therefore novel.

OPN from bovine milk has 28 phosphorylations (27× on serine and 1× on threonine), three O-glycosilations and no N-glycosilations [7]. Rat OPN isolated from bone has 13 phosphorylations (12× on serine and 1× on threonine) and additionally contains sulfate groups [8]. Recombinant OPN may undergo autophosphorylation on tyrosine. The differences in the number of phosphate groups in OPN from bovine milk and OPN from rat bone are presumably based on their different tissues of origin and not from the species, because the phosphorylation sites are very highly conserved in all OPN variants sequenced to date [7]. Sørensen et al have additionally found that the phosphorylation is almost 100%, i.e. all sites which are phosphorylated are always completely 100% phosphorylated [7]. We have detected OPN in the cerebrospinal fluid for the first time, which has never previously been described in the literature. We have moreover shown, interestingly, that DROPN-peptides with the same sequence but a different number of phosphorylations occur within the same sample of cerebrospinal fluid, which was not to be expected according to previous results of OPN in other body fluids and is novel. In addition, only the osteopontin protein has been detected to date in biological samples, but not osteopontin peptide fragments. During bone remodeling in rats, elevated osteopontin mRNA concentrations occur [9]. The connection between age and osteopontin expression is not clear because results of different studies describe both an increased and a reduced OPN expression in older compared with younger experimental animals [2, 9, 10].

One of the functions of OPN is presumably regulation of crystal growth during calcification processes, and the effect of OPN may be both to enhance and to inhibit calcium crystallization. In atherosclerosis there is not only calcification of the affected vessel walls but also remodeling of the extracellular matrix. Osteopontin can be detected immunohistologically preferentially in the calcified regions. [11] and there is expressed by macrophages and smooth muscle cells. Osteopontin might possibly serve to regulate vascular calcifications [11]. The direction in which osteopontin acts presumably depends on the microenvironment and the status of osteopontin in relation to its post-translational modifications, especially its phosphorylation [7]. Ek-Rylander et al were able to show, for example, that dephosphorylated OPN no longer assists osteoclast adhesion [12]. Dephosphorylation of OPN reduces the inhibitory activity of OPN on hydroxyapatite crystal formation, indicating a functional importance of OPN phosphorylation [13]. OPN inhibits crystal growth in the urine and thus prevents the development of bladder stones. Our results show, however, differing from the results described above, that both phosphorylated DROPN peptides and the corresponding non-phosphorylated DROPN peptides can be used as dementia markers in the same way through their elevated concentration. The markers of the invention are therefore fragments which do not correspond to that to be expected for OPN fragments in relation to their structural modification. Osteopontin presumably also mediates cell-cell and cell-matrix interaction, thus controlling the directed migration of immune cells, osteocytes and tumor cells ("homing") to various sites in the body. For this purpose, osteopontin interacts with CD44, a ubiquitously expressed transmembrane protein [4, 5]. Further ligands of CD44 besides osteopontin are vitronectin and hyaluronic acid. CD44-osteopontin interaction leads to cellular chemotaxis, while CD44-hyaluronic acid interaction leads to homotypic cell aggregation. It was possible to detect in vitro a chemotactic activity of osteopontin on astrocytes [14]. Osteopontin-deficient mice display disturbances of wound healing and of the regulation of the immune response [15]. It was additionally possible to show that macrophages in the vicinity of human tumors and in necrotic tumor regions, and in ischemic regions of the brain [14] express large amounts of osteopontin protein and mRNA, and osteopontin therefore presumably has an important function in matrix reorganization during wound healing.

Osteopontin promotes the adhesion and migration of vascular smooth muscle cells and endothelial cells. In gliomas, inter alia osteopontin and its receptor alpha V beta 3-integrin is induced via VEGF ("vasclar endothelial growth factor"), thus possibly inducing angiogenesis. In stroke, which is not a progressive, chronic dementia disease, it has been possible to show an increase in the OPN mRNA [16].

PREFERABLY EMBODIMENTS OF THE INVENTION

The dementia detected by the method of the invention is preferably a progressive, chronic dementia disease such as, for example, Alzheimer's disease. It has been possible to date to detect the change in the concentration of the peptides and peptide fragments of the invention in various dementia diseases such as, for example, Alzheimer's disease or vascular dementia. It can be concluded from this that the peptides of the invention can also be used for the detection and for the therapy of Alzheimer's disease and related neurological diseases. One embodiment of this method is the determination of dementia diseases at an early date, for example minimal cognitive impairment (MCI).

The identification is preferably concentrated on particular peptide fragments of the OPN protein with the GeneBank accession No. X13694 (SEQ ID NO: 32), i.e. on peptides which comprise partial sequences of the OPN protein or else on the OPN protein itself. These peptides (peptide fragments) are referred to as dementia related osteoponton (DROPN) peptides and are referred to hereinafter as DROPN-1 to DROPN-31 (SEQ ID NO: 1 to SEQ ID NO: 31). The connection between OPN protein and DROPN-1 to DROPN-31 (SEQ ID NO: 1 to SEQ ID NO: 31) is depicted in FIG. 1. The sequences we determined for the peptides are indicated in the sequence listing. These OPN fragments are produced naturally in nature and have not previously been described in the literature. These fragments are different from peptides as often described in the literature, produced by in vitro proteolysis through addition of proteases such as, for example, trypsin. They therefore represent novel, previously unknown substances. These peptides were initially concentrated and purified from biological samples by reverse phase chromatography and subsequently separated by mass spectrometry from other accompanying peptides, so that it was subsequently possible to sequence these DROPN peptides.

The sequences of the peptides in the single-letter amino acid code are as follows:

| DROPN SEQ ID NO. | OPN sequence (X13694 SEQ ID NO. 32) | Mono-isotopic theoret. mass (Da) | Sequence |
|---|---|---|---|
| 1 | 19–42 | 2627.2715 | VKQADSGSSEEKQLYNKYPDAVAT |
| 2 | 27$_{+r1}$–34$_{+r2}$ | ≧1009.4716 | r1-SEEKQLYN-r2 |
| 3 | 208–243 | 4032.7594 | AQDLNAPSDWDSRGKDSYETSQLDDQSAETHSHKQS |
| 4 | 208–246 | 4465.0079 | AQDLNAPSDWDSRGKDSYETSQLDDQSAETHSHKQSRLY |
| 5 | 211–243 | 3718.6368 | LNAPSDWDSRGKDSYETSQLDDQSAETHSHKQS |
| 6 | 231–245 | 1737.8030 | DDQSAETHSHKQSRL |
| 7 | 231–246 | 1900.8664 | DDQSAETHSHKQSRLY |
| 8 | 222$_{+r3}$–229$_{+r4}$ | ≧956.4087 | r3-KDSYETSQ-r4 |
| 9 | 234$_{+r5}$–241$_{+r6}$ | ≧895.4148 | r5-SAETHSHK-r6 |
| 10 | 249–314 | ** 7653.6003 | KANDESNEHSDVIDSQELSKVSREFHSHEFHSHEDMLVVDPKSKEEDKHLKFRISHELDSASSEVN |
| 11 | 249–288 | 4662.0953 | KANDESNEHSDVIDSQELSKVSREFHSHEFHSHEDMLVVD |
| 12 | 267–283 | 2093.9304 | SKVSREFHSHEFHSHED |
| 13 | 254$_{+r7}$–261$_{+r8}$ | ≧899.3985 | r7-SNEHSDVI-r8 |
| 14 | 271$_{+r9}$–278$_{+r10}$ | ≧1087.4835 | r9-REFHSHEF-r10 |
| 15 | 285–297 | 1522.7991 | LVVDPKSKEEDKH |
| 16 | 285–298 | 1635.8832 | LVVDPKSKEEDKHL |
| 17 | 285–299 | 1763.9781 | LVVDPKSKEEDKHLK |
| 18 | 285–300 | 1911.0466 | LVVDPKSKEEDKHLKF |
| 19 | 285–312 | 3222.6521 | LVVDPKSKEEDKHLKFRISHELDSASSE |
| 20 | 285–314 | 3435.7634 | LVVDPKSKEEDKHLKFRISHELDSASSEVN |
| 21 | 286–299 | 1650.8941 | VVDPKSKEEDKHLK |
| 22 | 286–300 | 1797.9625 | VVDPKSKEEDKHLKF |
| 23 | 286–312 | 3109.568 | WDPKSKEEDKHLKFRISHELDSASSE |
| 24 | 285–312 | 2796.4042 | PKSKEEDKHLKFRISHELDSASSE |
| 25 | 290$_{+r11}$–297$_{+r12}$ | ≧1112.5826 | r11-KSKEEDKHL-r12 |
| 26 | 303$_{+r13}$–310$_{+r14}$ | ≧844.3563 | r13-SHELDSAS-r14 |
| 27 | 19–41 | 2526.2238 | VKQADSGSSEEKQLYNKYPCAVA |
| 28 | 20–42 | 2528.2032 | KQADSGSSEEKQLYNKYPDAVAT |
| 29 | 211–243 | *** 3718.6368 | LNAPSDWDSRGKDSYETSQLDDQSAETHSHKQS |
| 30 | 251–285 | 4149.7995 | NDESNEHSDVIDSQELSKVSREFHSHEFHSHEDML |
| 31 | 251–284 | 4036.7154 | NDESNEHSDVIDSQELSKVSREFHSHEFHSHEDM |

* r1 represents a sequence which corresponds to the sequence or parts of the sequence of the OPN protein from amino acid 26 to 19, and r1 can be between 0 and 8 amino acids long, starting from amino acid 27 of the OPN protein. Correspondingly, r2 represents the OPN protein sequence from amino acid 35 to 42 or parts thereof, and r2 may be between 0 and 8 amino acids long starting from OPN amino acid 34. The other peptide chains r3 to r14 have compositions corresponding to the scheme explained above, with r3 corresponding maximally to OPN-221–208, r4 maximally to OPN-230–246, r5 maximally to OPN-233–208, r6 maximally to OPN-242–246, r7 maximally to OPN-253–249, r8 maximally to OPN-262–314, r9 maximally to OPN-270–249, r10 maximally to OPN-279–314, r11 maximally to OPN-289–249, r12 maximally to OPN-298–314, r13 maximally to OPN-302–249 and r14 maximally to OPN-311–314.
** For DROPN-10 (SEQ ID NO: 10) we were able to identify, in addition to the non-phosphorylated DROPN-10 (SEQ ID NO: 10) peptide, experimentally peptides having 1, 2, 3, 4 or 5 phosphate groups on the basis of their correspondingly increased masses. The masses determined experimentally for DROPN-10 (SEQ ID NO: 10) in this connection are: 7738/7818/7898/7978 and 8058 dalton. It has already been possible to determine one of the possible positions of the phosphate group in the monophosphorylated peptide DROPN-10 (SEQ ID NO: 10). The presumed position of the phosphate group in DROPN-10 (SEQ ID NO: 10) with one phosphate group is serine at position 291 of the OPN sequence, the presumed positions of the phosphate groups in DROPN-10 (SEQ ID NO: 10) with two phosphate groups are serine 275 and serine 291, the presumed positions of the phosphate groups in DROPN-10 (SEQ ID NO: 10) with three phosphate groups are serine 270, serine 275 and serine 291. The exact positions of the phosphate groups in DROPN-10 (SEQ ID NO: 10) with four or five phosphate groups is not yet known.
*** DROPN-29 (SEQ ID NO: 29) has a pyroglutamic acid as N-terminal modification.

Suitable Peptides

The peptides can exist in post-translational or chemical modification forms, thus influencing inter alia their masses and therefore the identification by mass spectrometry and also the elution behavior during chromatography, such as, for example, in reverse phase chromatography. In particular, the peptides may be in phosphorylated, glycosilated, sulfated, amidated, oxidized form or with an N-terminal pyroglutamic acid group etc. in the sample to be investigated.

The peptides are regarded as OPN peptides or DROPN peptides in particular when a maximum of 30% of their sequence differs from the sequence of the OPN protein. It is permissible in this connection for there to be point mutations, deletions, insertions and N-terminal and/or C-terminal extensions as long as the difference from the OPN protein sequence is no more than 30%.

It is to be assumed that the changes in concentration of the marker peptides (DROPN and OPN peptides) correlate with the severity of the disease and the stage of the neurological disease, especially of the progressive, chronically dementia disease, especially Alzheimer's disease. A further development of the invention therefore provides for using determination of the marker peptides also for determining the severity and the stage of the disease, in particular as replacement or supplement to carrying out a mini-mental state examination (MMSE). A further development of the invention additionally provides for using determination of the marker peptides for determining preliminary stages of neurolotical diseases, especially mild cognitive impairment (MCI), or for prognosis of the course of the disorder.

The control samples which are possibly used may constitute a pooled sample from various controls. The sample to be investigated may also be a pooled sample, and where there is a positive result individual investigations are subsequently carried out.

Suitable Biological Samples

The biological sample may preferably be (human) cerebrospinal fluid (CSF) or a sample such as serum, plasma, urine, stool, tear fluid, sputum, synovial fluid etc. This depends inter alia on the sensitivity of the chosen detection method (mass spectrometry, ELISA etc.). Serum, plasma and urine are particularly of interest because this sample material is often obtained without great effort from patients using standard investigations. It is also possible where appropriate to use homogenized tissue samples.

It is therefore provided in a further embodiment of this invention for tissue homogenates to be produced, for example from human tissue samples obtained in biopsies, for preparation of the sample to be investigated. These tissues can be comminuted for example with manual homogenizers, with ultrasound homogenizers or with electrically operated homogenizers such as, for example, Ultraturrax, and then be boiled in a manner known to the skilled worker in acidic aqueous solutions with, for example, 0.1 to 0.2 M acetic acid for 10 minutes. The extracts are then subjected to the respective detection method, e.g. a mass spectrometric investigation. The samples can be prepared, for example where appropriate diluted or concentrated, and stored in the usual way.

Use of the DROPN Peptides for Producing Diagnostic Agents

The invention further comprises the use of at least one of the DROPN peptides of the invention or of a OPN protein for the diagnosis of neurological diseases, especially chronic dementia diseases, especially of Alzheimer's disease, and the use of DROPN peptides for obtaining antibodies or other agents which, because of their DROPN peptide-specific binding properties, are suitable for developing diagnostic reagents for detecting these diseases. The invention also encompasses the use of DROPN peptides for obtaining phage particles which bind these peptides specifically, or which conversely present DROPN peptides on their surface and thus make it possible to identify binding partners such as, for example, receptors of OPN proteins or DRBPN peptides.

Detection Methods for DROPN Peptides

Various methods can be used for detecting the DROPN peptides within the framework of the invention. Methods suitable are those which make it possible to detect DROPN peptides specifically in a patient's sample. Suitable methods are, inter alia, physical methods such as, for example, mass spectrometry or liquid chromatography, molecular biology methods such as, for example, reverse transcriptase polymerase chain reaction (RT-PCR) or immunological detection techniques such as, for example, enzyme linked immunosorbent assays (ELISA).

Physical Detection Methods

One embodiment of the invention is the use of physical methods which are able to indicate the peptides of the invention qualitatively or quantitatively. These methods include, inter alia, mass spectrometry, liquid chromatography, thin-layer chromatography, NMR (nuclear magnetic resonance) spectroscopy etc. This entails comparison of quantitative measured results from a sample to be investigated with the measurements obtained in a group of patients suffering from neurological diseases, in particular chronic dementia diseases, preferably Alzheimer's disease, and a control group. It is possible to infer the presence of a neurological diseases, in particular a chronic dementia disease, in particular Alzheimer's disease, and/or the severity of this disease from these results.

In a preferred embodiment of this invention, the peptides in the sample are separated by chromatography before the identification, in particular preferably by reverse phase chromatography, with particular preference for separation of the peptides in the sample by high-resolution reverse phase high performance liquid chromatography (RP-HPLC). A further embodiment of this invention is the carrying out of precipitation reactions to fractionate the sample using precipitants such as, for example, ammonium sulfate, polyethylene glycol, trichloroacetic acid, acetone, ethanol etc. The fractions obtained in this way are subjected singly to the respective detection method, e.g. the investigation using mass spectrometry. A further embodiment of the invention is the use of liquid phase extraction. For this purpose, the sample is mixed with a mixture of an organic solvent such as, for example, polyethylene glycol (PEG) and an aqueous salt solution. Owing to their physical properties, particular constituents of the sample then accumulate in the organic phase, and others in the aqueous phase, and can thus be separated from one another and subsequently analyzed further.

Reverse Phase Chromatography

A particularly preferred embodiment of this invention encompasses the use of reverse phase chromatography, in particular a C18 reverse phase chromatography column using mobile phases consisting of trifluoroacetic acid and acetonitrile, for separation ofpeptides in human cerebrospinal fluid. For example the fractions collected in each case each comprise 1/100 of the mobile phase volume used. The fractions obtained in this way are analyzed with the aid of a mass spectrometer, preferably with the aid of a MALDI mass spectrometer (matrix-assisted laser desorption ionization) using amatix solution consisting of, for example, of L(−) fucose and alpha-cyano-4-hydroxycinnamic acid dissolved in a mixture of acetonitrile, water, trifluoroacetic acid and acetone, and thus the presence of particular masses is established and the signal intensity quantified. These masses correspond to the masses of the peptides DROPN-1 to DROPN-31 (SEQ ID NO:1 to SEQ ID NO:31 ) of the invention.

Mass Spectrometry

In a preferred embodiment of the invention, the peptide(s) can be identified with the aid of mass spectrometric determination, preferably a MALDI (matrix-assisted laser desorption and ionization) mass spectrometry. In this case, the mass spectrometric determination further preferably includes at least one of the following mass signals, in each case calculated on the basis of the theoretical monoisotopic mass of the corresponding peptide. It is possible for slight differences from the theoretical monoisotopic mass to show owing to the experimental error and the natural isotope distribution. In addition, in MALDI mass determinations a proton is added to the peptides owing to the method of measurement, whereby the mass increases by 1 dalton. The following masses correspond to the theoretical monoisotopic masses of the peptides identified by us, calculated with suitable software, in this case GPMAW 4.02. These theoretical monoisotopic masses may occur singly or in combination in a sample:

DROPN-1 (SEQ ID NO: 1)=2627.2715/DROPN-2(SEQ ID NO: 2)$\geq$1009.4716/DROPN-3 (SEQ ID NO: 3)=4032.7594/DROPN-4(SEQ ID NO: 4)=4465.0079/DROPN-5(SEQ ID NO: 5)=3718.6368/DROPN-6(SEQ ID NO: 6)=1737.8030/DROPN-7(SEQ ID NO: 7)=1900.8664/DROPN-8(SEQ ID NO: 8)$\geq$956.4087/DROPN-9(SEQ ID NO: 9)$\geq$895.4148/DROPN-10(SEQ ID NO: 10)=7653.6003/DROPN-11(SEQ ID NO: 11)=4662.0953/DROPN-12(SEQ ID NO: 12)=2093.9304/DROPN-13(SEQ ID NO: 13)$\geq$899.3985/DROPN-14(SEQ ID NO: 14)$\geq$1087.4835/DROPN-15(SEQ ID NO: 15)=1522.7991/DROPN-16(SEQ ID NO: 16)=1635.8832/DROPN-17(SEQ ID NO: 17)=1763.9781/DROPN-18(SEQ ID NO: 18)=1911.0466/DROPN-19(SEQ ID NO: 19)=3222.6521/DROPN-20(SEQ ID NO: 20)=3435.7634/DROPN-21(SEQ ID NO: 21)=1650.8941/DROPN-22(SEQ ID NO: 22)=1797.9625/DROPN-23(SEQ ID NO: 23)=3109.5680/DROPN-24(SEQ ID NO: 24)=2796.4042/DROPN-25(SEQ ID NO: 25)$\geq$1112.5826/DROPN-26(SEQ ID NO: 26)$\geq$844.3563/DROPN-27(SEQ ID NO: 27)=2526.2238/DROPN-28(SEQ ID NO: 28)=2528.2031/DROPN-29(SEQ ID NO: 29)=3718.6368/DROPN-30(SEQ ID NO: 30)=4149.7995 and DROPN-31(SEQ ID NO: 31)=4036.7154 dalton.

The symbol $\geq$ (is greater than or equal to) is to be understood to mean here that the relevant DROPN peptides cannot have any larger masses but can have only the masses possible owing to the amino acids which are possibly additionally present at the ends of these peptides. Amino acids which may be additionally present at the ends of these peptides are not just any ones but only those which may be present at this sequence position owing to the sequence of the OPN protein.

Mass Spectrometric Determination of the Sequence of the DROPN Peptides

For the further practical application of this embodiment, further confirmation of the result of detection is advisable and possible by establishing the identity of the peptides corresponding to the masses, taking account exclusively of peptide signals which may be derived from an OPN protein. This confirmation takes place by identifying the peptide signals preferably using methods of mass spectrometry, e.g. MS/MS analysis [17].

Novel, specific peptides of OPN proteins (DROPN peptides) were identified, and their significance was revealed by the method of the invention. These DRDPN peptides and their derivatives are referred to herein as DROPN-1 to DROPN-31 (SEQ ID NO: 1to SEQ ID NO: 31). Their sequences are indicated in the sequence listing. The DROPN peptides DROPN-2, -8, -9, -13, -14, -25 and DROPN-26 (SEQ ID NOS: 2, 8, 9, 13, 14, 25 and 26) may comprise on the N and/or C terminus additional amino acids corresponding to the corresponding sequence of the relevant OPN protein. The invention also encompasses the DROPN peptides prepared recombinantly or synthetically, and isolated from biological samples, in unmodified, chemically modified or post-translationally modified form. In this connection, two point mutations and other differences are possible as long as the DROPN peptide has at least 8 amino acids which agree in their identity and their position within the peptide sequence with an OPN protein.

Molecular Biology Detection Techniques

Finally, the invention also encompasses nucleic acids which correspond to DROPN peptides, and especially those which correspond to the DROPN peptides of the invention, the use thereof for the indirect determination and quantification of the relevant OPN proteins and peptides. This also includes nucleic acids which represent, for example, non-coding sequences such as, for example, 5'- or 3'-untranslated regions of the mRNA, or nucleic acids which show a sequence agreement with the OPN nucleic acid sequence which is sufficient for specific hybridization experiments and which are therefore suitable for the indirect detection of relevant proteins, especially the DROPN peptides.

One exemplary embodiment thereof encompasses the obtaining of tissue samples, e.g. of biopsy specimens, from patients and the subsequent determination of the concentration of an RNA transcript corresponding to the gene having the GeneBank accession No. X13694 (SEQ ID NO: 32) or corresponding to homologous OPN variants. This entails comparison of quantitative measured results (intensities) from a sample to be investigated with the measurements obtained in a group of patients suffering from Alzheimer's disease and a control group. Methods which can be used for the quantification are, for example, reverse transcriptase polymerase chain reaction (RT-PCR), quantitative real-time PCR (ABI PRISM® 7700 Sequence Detection System, Applied Biosystems, Foster City, Calif., USA), in situ hybridization or Northern blots in a manner known to the skilled worker. The presence of a chronic dementia disease, preferably Alzheimer's disease and/or the severity thereof can be inferred from the results.

Immunological Detection Methods

In a further preferred embodiment of the invention, the DROPN peptides or the OPN proteins can be identified using an immunological detection system, preferably an ELISA (enzyme linked immuno sorbent assay). This immunological detection picks up at least one DROPN peptide or OPN protein. To increase the specificity, it is also possible and preferred to use the so-called sandwich ELISA in which the detection of the DROPN peptides depends on the specificity of two antibodies which recognize different epitopes within the same molecule. However, it is also possible to use other ELISA systems, e.g. direct or competitive ELISA, to detect DROPN peptides or OPN proteins. Other ELISA-like detection techniques such as, for example, RIA (radio immuno assay), EIA (enzyme immuno assay), ELI-Spot etc. are also suitable as immunological detection systems. DROPN peptides or OPN proteins isolated from biological samples, recombinantly prepared or chemically synthesized can be used as standard for the quantification. Identification of the DROPN peptide(s) is generally possible for example with the aid of an antibody directed to the DROPN peptide or OPN protein. Further methods suitable for such detections are, inter alia, Western blotting, immunoprecipitation, dot-blots, plasmon resonance spectrometry (BIACORE® technology, Biacore International AB, Uppsala, Sweden), phage particles, PNAs (peptide nucleic acids), affinity matrices (e.g. ABICAP technology, ABION Gesellschaft für Biowissenschaften und Technik mbH, Jülich, Germany) etc. Substances/molecules suitable as detection agents are generally all those permitting the construction of a specific detection system because they specifically bind a DROPN peptide or OPN protein.

Obtaining of DROPN Peptides and Anti-DROPN Peptide Antibodies

A further embodiment of the invention is the obtaining of DROPN peptides using recombinant expression systems, chromatographic methods and chemical synthesis protocols which are known to the skilled worker. The DROPN peptides obtained in this way can be used inter alia as standards for quantifying the respective DROPN peptides or as antigen for producing DROPN peptide antibodies. Methods known to the skilled worker and suitable for isolating and obtaining DROPN peptides include the recombinant expression of peptides. It is possible to use for the expression of the DROPN peptides inter alia cell systems such as, for example, bacteria such as *Escherichia coli,* yeast cells such as *Saccharomyces cerevisiae,* insect cells such as, for example, *Spodoptera frugiperda* (Sf-9) cells, or mammalian cells such as Chinese Hamster Ovary (CHO) cells. These cells are obtainable from the American Tissue Culture Collection (ATCC). For recombinant expression of DROPN peptides, for example nucleic acid sequences which code for DROPN peptides are inserted in; combination with suitable regulatory nucleic acid sequences such as, for example, promoters, antibiotic selection markers etc. into an expression vector by molecular biology methods. A vector suitable for this purpose is, for example, the vector pcDNA3.1 from Invitrogen. The DROPN peptide expression vectors obtained in this way can then be inserted into suitable cells, e.g. by electroporation. The DROPN peptides produced in this way may be C- or N-terminally fused to heterologous sequences of peptides such as polyhistidine sequences, hemagglutinin epitopes (HA tag), or proteins such as, for example, maltose-binding proteins, glutathione S-transferase (GST), or protein domains such as the GAL-4 DNA binding domain or the GAL4 activation domain. The DROPN peptides can be prepared by chemical synthesis for example in accordance with the Merrifield solid-phase synthesis protocol using automatic synthesizers which are obtainable from various manufacturers.

A further embodiment of this invention is the isolation of DROPN peptides from biological samples or cell culture media or cell lysates from recombinant expression systems, e.g. using reverse phase chromatography, affinity chromatography, ion exchange chromatography, gel filtration, isoelectric focusing, or using other methods such as preparative immunoprecipitation, ammonium sulfate precipitation, extraction with organic solvents etc. A further embodiment of the invention is the obtaining of monoclonal or polyclonal antibodies using DROPN peptides. The obtaining of antibodies takes place in the conventional way familiar to the skilled worker. A preferred embodiment of the production and obtaining of DROPN peptide-specific antibodies, and a particularly preferred embodiment is the production of DROPN peptide-specific antibodies which recognize neoepitopes, i.e. epitopes which are present only on DROPN peptides but not in an OPN protein. Such anti-DROPN peptide antibodies make the specific immunological detection of DROPN peptides possible in the presence of OPN protein. Polyclonal antibodies can be produced by immunizations of experimental animals such as, for example, mice, rats, rabbits or goats. Monoclonal antibodies can be obtained for example by immunizations of experimental animals such as, for example mice or rats and subsequent application of hybridoma techniques or else via recombinant experimental approaches such as, for example, via antibody libraries such as the HuCAL® antibody library of MorphoSys, Martinsried, Germany, or other recombinant production methods known to the skilled worker. Antibodies can also be used in the form of antibody fragments such as, for example, Fab fragments or Fab2 fragments etc.

Therapy Development and Monitoring Through DROPN Peptide Determinations

A further exemplary use is the quantitative or qualitative determination of the abovementioned DROPN peptides or OPN proteins for estimating the efficacy of a therapy under development for neurological diseases, in particular chronic dementia diseases, in particular Alzheimer's disease. The invention can also be used to identify suitable patients for clinical studies for developing therapies for these diseases, in particular Alzheimer's disease. This entails comparison of quantitative measured results from a sample to be investigated with the measurements obtained in a control group and a group of patients. The efficacy of a therapeutic agent, or the suitability of the patient for a clinical study, can be inferred from these results. The testing of efficacy and the selection of the correct patients for therapies and for clinical studies is of outstanding importance for successful application and development of a therapeutic agent, and no clinically measurable parameter making this reliably possible is yet available for Alzheimer's disease [18].

Examination of the Therapeutic Efficacy of OPN Proteins, DROPN Peptides and of Agents which Modulate the Expression and the Bioavailability of these Substances One exemplary embodiment thereof encompasses the cultivation of cell lines and their treatment with OPN proteins, DROPN peptides or with substances which promote the expression of OPN protein or promote the processing of OPN protein to DROPN peptides, such as, for example, proteases which recognize dibasic sequence motifs'. It is possible thereby to establish the biological properties of OPN protein and DROPN peptides in connection with neurological diseases, in particular Alzheimer's disease. Fusion proteins and fusion peptides can also be used for the treatment of the cell lines, e.g. fusion proteins with peptide sequences which promote transport of the fusion protein into the interior of the cell. Examples of possible fusion partners are HIV TAT sequences or antennapedia sequences etc. It is likewise possible to transfect cell lines with expression vectors which bring about, directly or indirectly, expression of OPN protein or DROPN peptides by the transfected cells. These expression vectors may code inter alia for DROPN peptides or OPN proteins. Simultaneous transfections with different DROPN peptides and/or OPN proteins can also be carried out. Alternatively, suitable cell lines can be treated with anti-OPN protein or anti-DROPN peptide antibodies or with nucleic acids which suppress the expression of OPN, such as, for example, OPN antisense nucleic acids, OPN triplex nucleic acids or ribozymes directed against OPN mRNA. Cell lines which appear suitable as neurological model systems in connection with OPN in particular can be used for such investigations. Read-out systems which can be used for these investigations are inter alia tests which measure the rate of proliferation of the treated cells, their metabolic activity, the rate of apoptosis of the cells, changes in cell morphology, in the expression of cell-intrinsic proteins or reporter genes or which measure the release of cytosolic cell constituents as markers for cell death. Further test systems which can be used are suitable strains of experimental animals, e.g. of mice or rats, which are considered as model of neurological diseases, in particular as model of Alzheimer's disease. These experimental animals can be used to investigate the efficacy of therapeutic strategies which aim to modulate the concentration of DROPN peptides or of OPN proteins. It is additionally possible to investigate proteins and peptides such as, for example, OPN proteins or DROPN peptides in experimental animals, it being possible for these peptides and proteins in some circumstances to be pharmaceutically processed so that they are better able to cross the blood-brain barrier and/or the blood-CSF barrier. It is possible to use as pharmaceutical processing method inter alia liposome-packaged proteins and peptides, proteins and peptides covalently fused to or non-covalently associated with transport peptides such as, for example, an HIV TAT sequence etc. In addition, peptides and proteins can be chemically modified in such a way that they acquire more lipophilic properties and are therefore able to penetrate more easily into cells. Peptides which are only slightly soluble in aqueous solutions can conversely be chemically modified so that they become more hydrophilic and then can be used for example as intravenously injectable therapeutic agent. Acid-resistant capsules can be used to protect sensitive substances, intended for oral administration, in the stomach.

Read-out parameters in experiments with animal models may be the survival time of the animals, their behavior, their short-term memory and their learning ability. One example of a memory test which is suitable for experimental animals is the Morris water maze test. Further parameters which can be used are the determination of body function such as, for example, blood tests, measurement of brain currents, metabolism tests, the rate of expression of OPN proteins and DROPN peptides and other proteins associated with the disease, and morphological and histological investigations on tissues such as, for example, the brain.

The Invention is Illustrated in Detail Below by Means of Examples Reference is also made to the Figures in this Connection.

FIG. 1: Alignment of the DROPN peptides with their the OPN protein

FIG. 2: Reverse phase chromatography for separation and enrichment of DROPN peptides from cerebrospinal fluid FIG. 3: Mass spectrometry measurement (MALDI) on DROPN-1 (SEQ ID NO:1) as example FIG. 4: MALDI as relatively quantifying mass spectroscopic method FIG. 5: MS/MS fragment spectrum of the peptide DROPN-10 (SEQ ID NO:10) with one phosphate group as example.

Figure 6A:
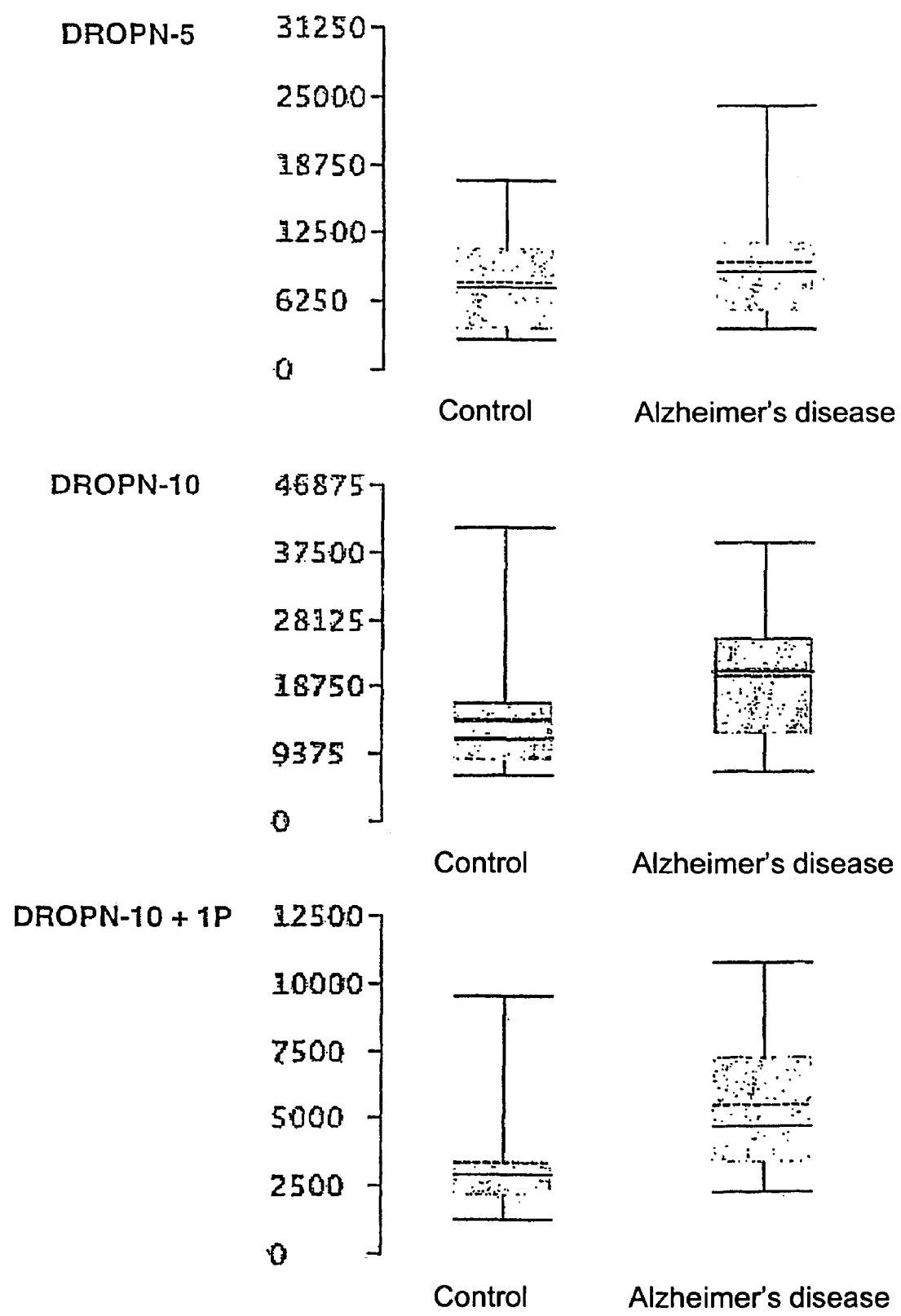
Figure 6B:
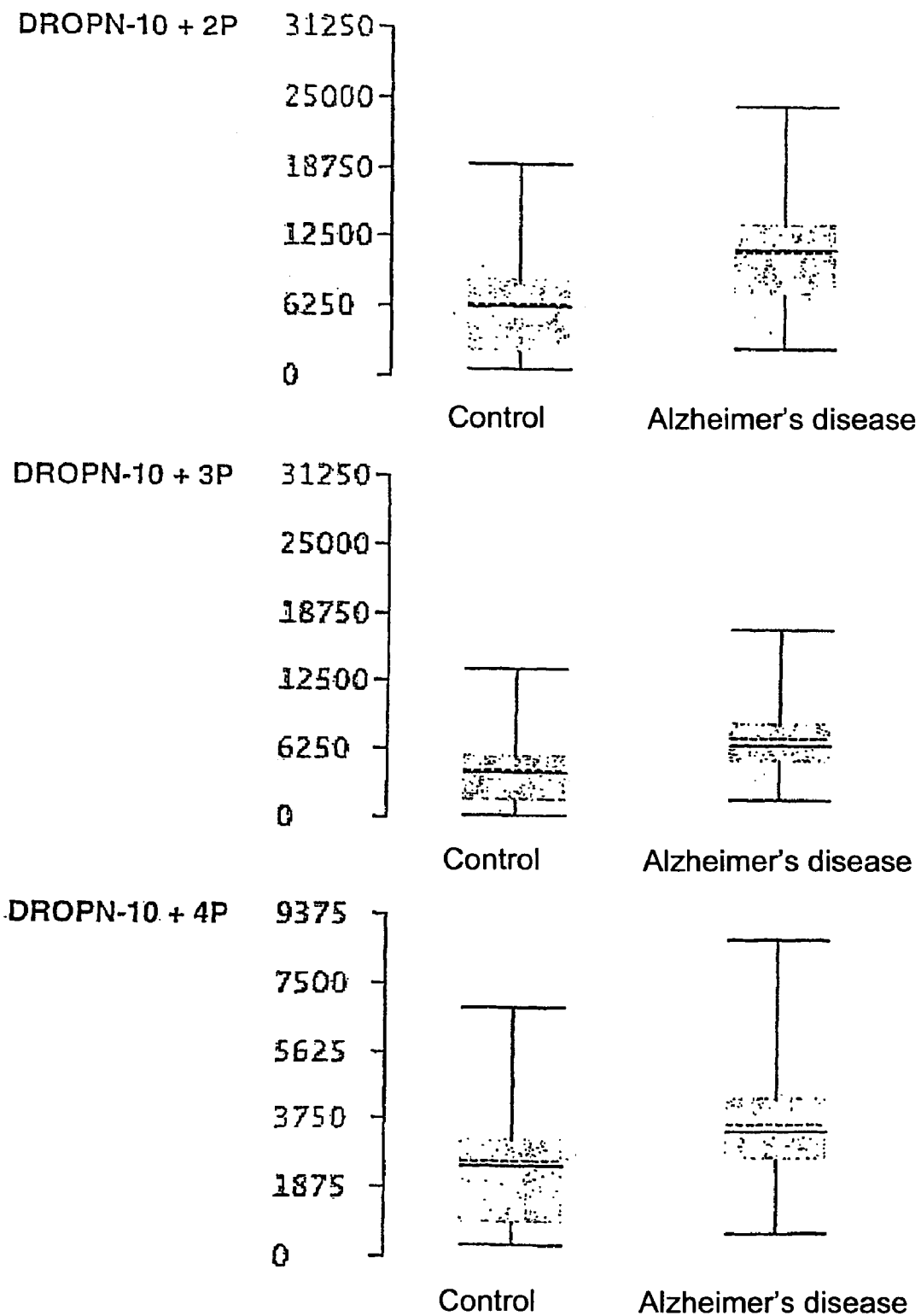
Figure 6C:
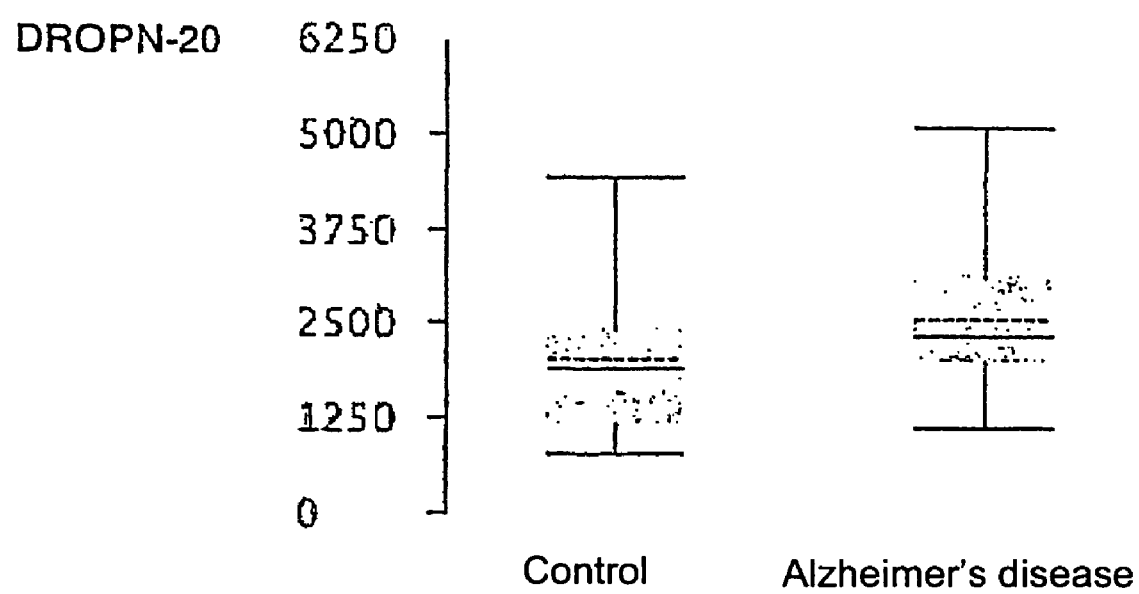

FIGS. 6A–C: Box-whisker plots for quantitative comparison of the concentrations of DROPN-5 (SEQ ID NO:5), DROPN-10(SEQ ID NO:10) and DROPN-20 (SEQ ID NO:20) in patients with Alzheimer's disease compared with control patients.

Figure 7:
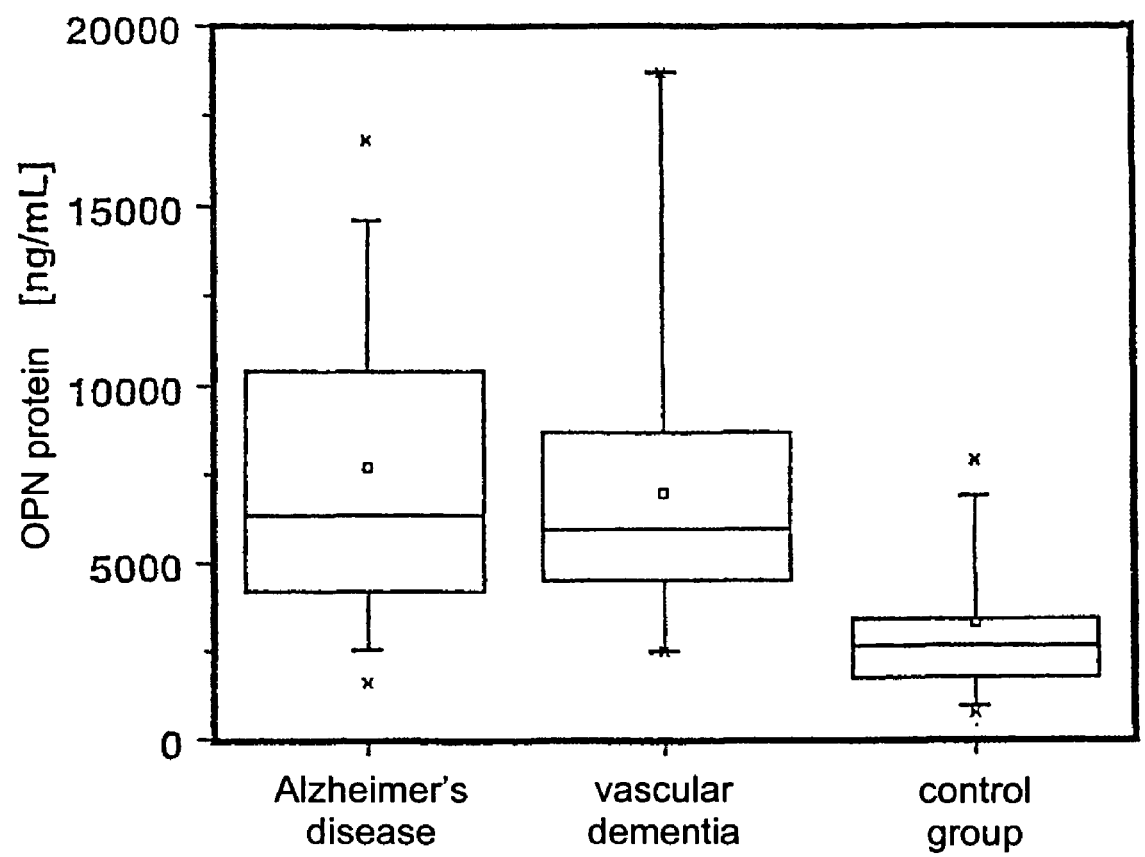

FIG. 7: Determination of the concentration of the OPN protein in cerebrospinal fluid using a sandwich ELISA.

FIG. 1 shows an alignment of the OPN peptides of the invention with their the OPN protein. The theoretical monoisotopic masses of the peptides, stated in dalton, were calculated using the GPMAW 4.02 software. These are: DROPN-1 (SEQ ID NO:1)=2626.2715/DROPN-2 (SEQ ID NO:2)≧1009.4716/DROPN-3(SEQ ID NO:3)=4032.7594/ DROPN-4 (SEQ ID NO:4)=4465.0079/DROPN-5 (SEQ ID NO:5)=3718.6368/DROPN-6 (SEQ ID NO:6)=1737.8030/ DROPN-7 (SEQ ID NO:7)=1900.8664/DROPN-8 (SEQ ID NO:8) 955.4087/DROPN-9 (SEQ ID NO:9) ≧895.4148/ DROPN-10 (SEQ ID NO:10)=7653.6003 DROPN-11 (SEQ ID NO:11)=4662.0953/DROPN-12 (SEQ ID NO:12)= 2093.9304/DROPN-13 (SEQ ID NO:13)≧899.3985/ DROPN-14 (SEQ ID NO:14)≧1087.4835/DROPN-15 (SEQ ID NO:15)=1522.7991/DROPN-16 (SEQ ID NO:16)=1635.8832/DROPN-17 (SEQ ID NO:17)=1763.5781/DROPN-18 (SEQ IDNO:18)=1911. 0466/DROPN-19 (SEQ ID NO:19)=3222.6521 DROPN-20 (SEQ ID NO:20)=3435.7634/DROPN-21 (SEQ ID NO:21)=1650.8941/DROPN-22 (SEQ ID NO:22)=1797. 9625/DROPN-23 (SEQ ID NO:23)=3109.5680/DROPN-24 (SEQ ID NO:24)=2796.4042/DROPN-25 (SEQ ID NO:25)≧1112.5826/DROPN-26 (SEQ ID NO:26)≧844. 3563/DROPN-27 (SEQ ID NO:27)=2526.2238/DROPN-28 (SEQ ID NO:28)=2528.2031/DROPN-29 (SEQ ID NO:29)=3718.6368/DROPN-30 (SEQ ID NO:30) 5=4149.7995 and DROPN-31 (SEQ ID NO:31)=4036.7154 dalton. The masses actually identified in the mass spectrometer differ from these theoretical, monoisotopic masses because of the natural isotope distribution and of a small measurement inaccuracy not exceeding 500 ppm. In addition, the measured mass for all the peptides is also increased owing to the MALDI measurement method used by the mass of a proton (=1 dalton). It was additionally possible to identify and determine experimentally peptide variants having 1 to 5 phosphate groups for DROPN-10 (SEQ ID NO:10). The masses experimentally determined for DROPN-10 (SEQ ID NO:10) in this connection are: 7738/ 7818/7898/7978 and 8058 dalton, with the mass of DROPN-10 (SEQ ID NO:10) being increased sequentially in each case by the mass of a phosphate group.

FIG. 2 shows an eluation profile of a with reverse phase chromatography as in Example 2 for the separation and concentration of the DROPN peptides from cerebrospinal fluid.

Figure 3:
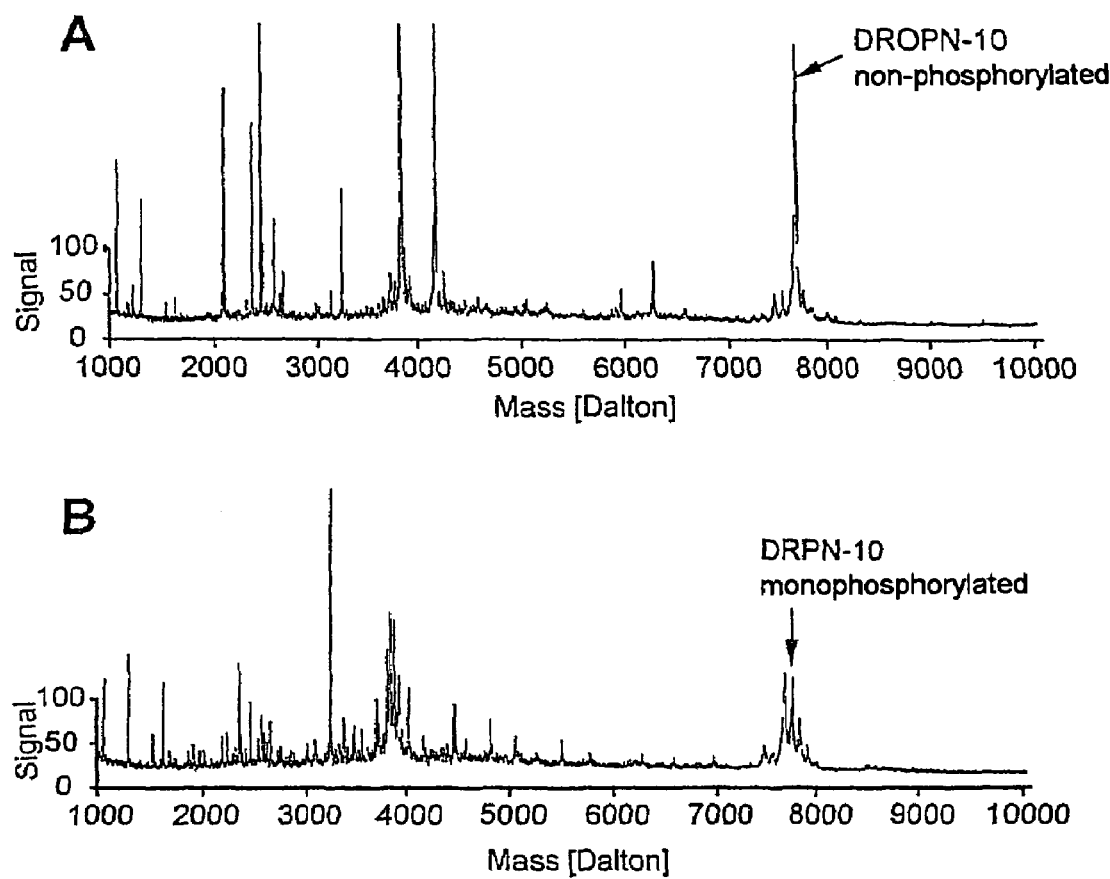

FIG. 3 shows a spectrum produced by MALDI mass spectrometric measurement as in Example 3 of DROPN-10 (SEQ ID NO:10) after reverse phase chromatography of human cerebrospinal fluid as in Example 2. DROPN-10 (SEQ ID NO:10) corresponds to the OPN sequence from amino acid 249–314. FIG. 3A shows the MALDI mass spectrum of DROPN-10 (SEQ ID NO:10) in its non-phosphorylated form. The mass peak of DROPN-10 (SEQ ID NO:10) is marked by an arrow. FIG. 3B shows the MALDI mass spectrum of a DROPN-10 (SEQ ID NO:10) variant containing one phosphate group. The mass peak of DROPN-10 (SEQ ID NO:10) 1× phosphate is marked by an arrow.

Figure 4:
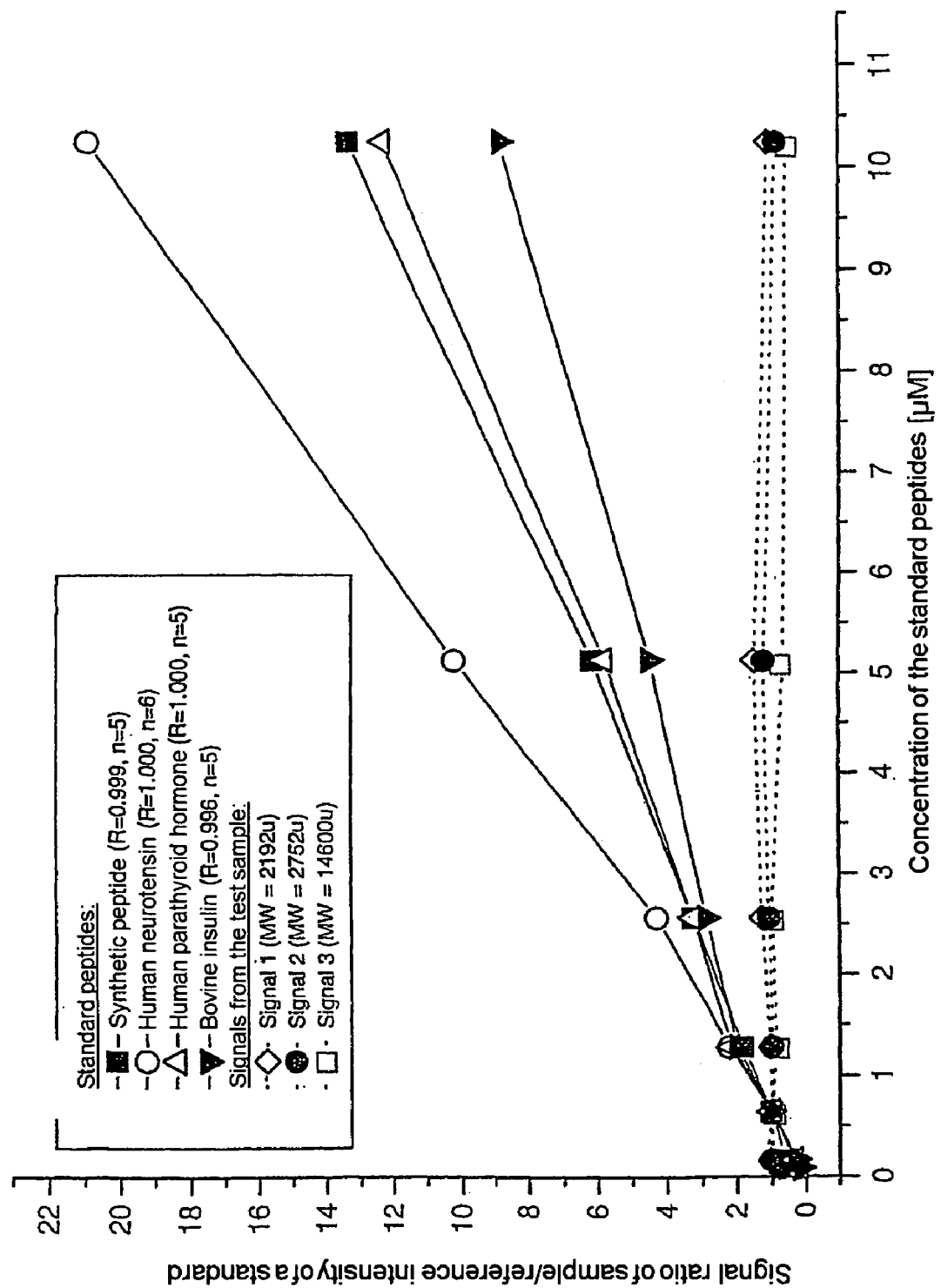

FIG. 4 shows data generated by MALDI as relatively quantifying MS method. A sample was mixed with different amounts of various standard peptides, and the intensity both of the standard signals and of representative sample signals was determined. All signal intensities of the standards were standardized to their signal intensity at a concentration of 0.64 μM (=1). Each peptide shows an individual typical ratio of signal strength to concentration, which can be read off in this diagram from the gradient of the plot.

Figure 5:
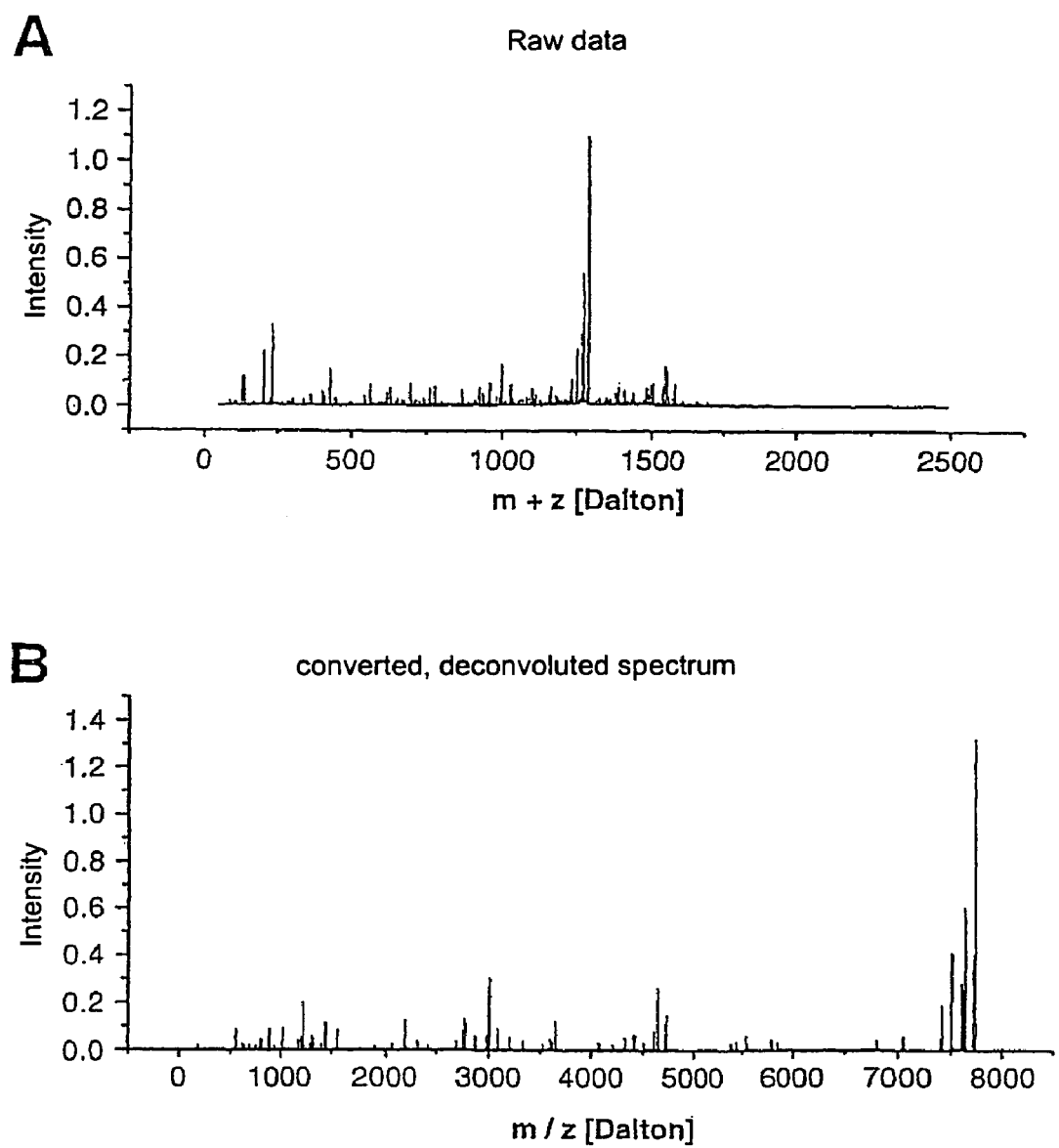

FIG. 5 shows an MS/MS fragment spectrum as in Example 4 of the peptide DROPN-10 (SEQ ID NO:10 of the invention having one phosphate group.

Upper trace: raw data of the measurement.

Lower trace: converted, deconvoluted mass spectrum of DROPN-10 (SEQ ID NO:10) having one phosphate group.

The peak pattern is characteristic of DROPN-10 (SEQ ID NO: 10) having one phosphate group.

DROPN-10 (SEQ ID NO:10) corresponds to the OPN sequence from amino acid 249–314.

FIG. 6 shows box-whisker plots for quantitative comparison of the concentrations of DROPN-5 (SEQ ID NO:5), DROPN-10 (SEQ ID NO:10) and DROPN-20 (SEQ ID NO:20) in patients with Alzheimer's disease compared with control patients, showing box-whisker plots for the non-phosphorylated and for mono-, di-,tri- and tetraphosphorylated DROPN-10 (SEQ ID NO:10) peptide. The figures show, in the form of box-whisker plots, a comparison of the integrated MALDI mass spectrometric signal intensities.

FIG. 7 shows the results of measurement of the concentrations of the OPN protein in cerebrospinal fluid determined using a sandwich ELISA, depicted as box plot. The right-hand half of the figure shows the results of the samples of patients with Alzheimer's disease, the middle part of the figure shows the results with samples from patients with vascular dementia and the left-hand part of the figures shows the results of the control group.

EXAMPLE 1

Obtaining Cerebrospinal Fluid for Determining DROPN Peptides

CSF or cerebrospinal fluid (fluid of the brain and spinal cord) is the fluid which is present in the four ventricles of the brain and in the subarachnoid space and which is produced in particular in the choroid plexus of the lateral ventricle. Cerebrospinal fluid is usually taken by lumbar puncture and less often by suboccipital puncture or ventricular puncture. In lumbar puncture (spinal puncture), to take cerebro-spinal fluid, the puncture involves penetration of the spinal subarachnoid space between the 3rd and 4th or the 4th and 5th lumbar spinous process with a long hollow needle, and thus CSF being obtained. The sample is then centrifuged at 2000×g for 10 minutes, and the supernatant is stored at −80° C.

EXAMPLE 2

Separation of Peptides in Cerebrospinal Fluid (CSF) for Mass Spectrometric Measurement of DROPN Peptides For the detection of OPN peptides in CSF by mass spectrometry, it is necessary in this example to separate the peptide constituents. This sample pretreatment serves to concentrate the peptides of the invention and to remove components which may interfere with the measurement. The separation method carried out is a reverse phase chromatography. Various RP chromatography resins and eluants are equally suitable for this. The separation of OPN peptides using a C18 reverse phase chromatography column with the size of 4 mm×250 mm supplied by Vydac is [lacuna] by way of example below. Mobile phases of the following composition were used: mobile phase A: 0.06% (v/v) trifluoroacetic acid, mobile phase B: 0.05% (v/v) trifluoroacetic acid, 80% (v/v) acetonitrile. Chromatography took place at 33° C. using an HP ChemStation 1100 supplied by Agilent Technologies with a micro flow cell supplied by Agilent Technologies. Human cerebrospinal fluid was used as sample. 440 μl of CSF were diluted with water to 1650 μl, the pH was adjusted to 2–3, the sample was centrifuged at 18 000×g for 10 minutes and finally 1500 μl of the sample prepared in this way were loaded onto the chromatography column. The chromatography conditions were as follows: 5% mobile phase B at time 0 min, from time 1 to 45 min continuous increase in the mobile phase B concentration to 50%, from time 45 to 49 min continuous increase in the mobile phase B concentration to 100% and subsequently up to time 53 min constant 100% buffer B. Collection of 96 fractions each of 0.5 ml starts 10 minutes after the start of the chromatography. The chromatogram of a cerebrospinal fluid sample prepared under the experimental conditions described herein is depicted in FIG. 2.

EXAMPLE 3

Measurement of Masses of Peptides by Means of MALDI Mass Spectrometry

For mass analysis, typical positive ion spectra of peptides are produced in a MALDI-TOF mass spectrometer (matrix-assisted laser desorption ionization). Suitable MALDI-TOF mass spectrometers are manufactured by PerSeptive Biosystems Framingham (Voyager-DE, Voyager-DE PRO or Voyager-DE STR) or by Bruker Daltonik Bremen (BIFLEX). The samples are prepared by mixing them with a matrix substance which typically consists of an organic acid. Typical matrix substances suitable for peptides are 3,5-dimethoxy-4-hydroxycinnamic acid, α-cyano-4-hydroxycinnamic acid and 2,5-dihydroxybenzoic acid. A lyophilized equivalent obtained by reverse phase chromatography and corresponding to 500 μl of human cerebrospinal fluid is used to measure the DROPN peptides of the invention. The chromatographed sample is dissolved in 15 μl of a matrix solution. This matrix solution contains, for example, 10 g/l α-cyano-4-hydroxycinnamic acid and 10 g/l L(−)fucose dissolved in a solvent mixture consisting of acetonitrile, water, trifluoroacetic acid and acetone in the ratio 49:49:1:1 by volume. 0.3 μl of this solution is transferred to a MALDI carrier plate, and the dried sample is analyzed in a Voyager-DE STR MALDI mass spectrometer from PerSeptive Biosystems. The measurement takes place in linear mode with delayed extraction™. An example of a measurement of one of the DROPN peptides of the invention is shown in FIG. 3.

The MALDI-TOF mass spectrometry can be employed to quantify peptides such as, for example, the DROPN peptides of the invention if these peptides are present in a concentration which is within the dynamic measurement range of the mass spectrometer, thus avoiding detector saturation. This is the-case for the measurement of the DROPN peptides of the invention in cerebrospinal fluid at a CSF equivalent concentration of 33.3 μl per μl of matrix solution. There is a specific ratio between measured signal and concentration for each peptide, which means that the MALDI mass spectrometry can preferably be used for the relative quantification of peptides. This situation is depicted in FIG. 4. If various amounts of different standard peptides are added to a sample, it is possible to measure the intensity both of these standard signals and of the sample signals. FIG. 4 shows by way of example a MALDI measurement as relatively quantifying MS method. All signal intensities of the standards were standardized to their signal intensity at a concentration of 0.64 μM (=1). Each peptide shows an individual, typical ratio of signal strength to concentration, which can be read off from the gradient of the plot.

EXAMPLE 4

Mass Spectrometric Identification of the DROPN Peptides

For quantification of the DROPN peptides of the invention it is necessary to ensure that the mass signals to be analyzed of peptides in the fractions obtained by reverse phase chromatography of cerebrospinal fluid, as in Example 2, in fact relate to the DROPN peptides of the invention.

The peptides of the invention are identified in these fractions for example using nanoSpray-MS/MS [17]. This entails a DROPN peptide ion in the mass spectrometer being selected in the mass spectrometer on the basis of its specific m/z (mass/charge) value in a manner known to the skilled worker. This selected ion is then fragmented by supplying collisional energy with an impinging gas, e.g. helium or nitrogen, and the resulting DROPN peptide fragments are detected in the mass spectrometer in an integrated analysis unit, and corresponding m/z values are determined (principle of tandem mass spectrometry) [19]. The fragmentation behavior of peptides makes unambiguous identification of the DROPN peptides of the invention possible when the accuracy of mass is, for example, 50 ppm by the use of computer-assisted search methods [20] in sequence databases into which the sequence-of an OPN protein has been entered. In this specific case, the mass spectrometric analysis took place with a quadrupole TOF Instrument, QStar-Pulsar model from Applied Biosystems-Sciex, USA. Examples of MS/MS fragment spectra are shown in FIG. 5.

Example 5

Mass Spectrometric Quantification of DROPN Peptides to Compare Their Relative Concentration in Control Samples Compared with Patients' Samples A sample preparation as in Example 1 and 2 followed by a MALDI measurement of the DROPN peptides of the invention as in Example 3 were carried out on 222 clinical samples, i.e. 82 control samples and 130 samples from patients suffering from Alzheimer's disease. Examples of MALDI signal intensities are depicted in the form of box-whisker plots in FIGS. 6A to 6C. The box-whisker plots depicted in FIG. 6 are based on measurements carried out in each case on 29 to 45 samples from Alzheimer's disease patients, and 13 to 44 control samples per experiment. A total of 4 experiments was carried out. The box-whisker plots depicted make it possible to compare the integrated MALDI mass spectrometric signal intensities of various DROPN peptides in controls with the MALDI signal intensities in samples from Alzheimer's disease patients. In these, the box, i.e. the columns in the diagrams in FIGS. 6A to 6C, in each case includes the range of MALDI signal intensities in which 50% of the respective MALDI signal intensities are to be found, and the lines starting from the box and pointing upward and downward (whiskers) indicate the range in which in each case the 25% of measurements which show the highest signal intensities (upper quartile) are to be found, and in which the 25% of measurements. which show the lowest signal intensities (lower quartile) are to be found. The full line in the columns indicates the median and the broken line in the columns indicates the mean.

EXAMPLE 6

Quantification of the OPN Protein with an Enzyme-Linked Immunosorbent Assay (ELISA) in Human Cerebrospinal Fluid from Patients' and Control Samples 20 cerebrospinal fluid samples from patients suffering from progressive, chronic dementia diseases and 12 samples from control subjects were diluted 1:50 with incubation buffer (140 mM NaCl, 2.7 mM KCl, 1.2 mM $KH_2PO_4$, 8 mM $Na_2HPO_4$ 1% bovine serum albumin, 0.05% Tween 20) and 100 μm of the samples diluted in this way were put in duplicates in ELISA plates coated with anti-human OPN antibody 017 (rabbit immunoglobulin G), and incubated at 37° C. for 1 h. After washing 7 times with 200 μl of washing buffer (0.05% Tween 20 in phosphate buffer) each time, 100 μl per well of the secondary antibody which is covalently coupled to the enzyme horseradish peroxidase (clone 10A16, monoclonal mouse immunoglobulin G antibody) were incubated in a concentration of 1 μg/ml in incubation buffer at 4° C. for 5.5 h, subsequently again washed 9 times with washing buffer, and a solution of 0.2 mg/ml tetra-methylbenzidine (TMB, Sigma) in substrate buffer (50 mM $Na_2HPO_4$, 20 mM citric acid, pH 5.0) was added as substrate and incubated at room temperature with exclusion of light for 30 min. The enzymatic reaction was stopped by adding 100 μl of stop solution (0.5 M $H_2SO_4$) per well, and subsequently the absorption was measured at 450 nm in a SUNRISE model spectrophotometer from TECAN. A standard series of known concentrations prepared with recombinant OPN was determined in the ELISA in parallel and used for the quantification. All the reagents used for the ELISA were purchased from IBL Hamburg. The OPN concentrations in the cerebrospinal fluid samples, calculated on the basis of the known concentrations of the standards, are depicted in the form of box plots in FIG. 7. Each box includes 50% of the data points with the statistical median as middle line. The upper and lower line of the box indicate the limits for ±25% of the data population. The line above the upper box is referred to as upper quartile UQ, and the lower line of the lower box is referred to as lower quartile LQ. The interquartile distance (IQD) indicates the distance of lower and upper quartile. The lines connected to the top and bottom of the box indicate the distance to the minimum and maximum respectively. Data points identified as outliers are excluded from this. This is the case when the value of a data point W>UQ+1.5*IQD or W<LQ−1.5*IQD.

The headings in this document are intended merely to provide structure to the text. They are not intended to limit or restrict the matters described. All the examples are intended to characterize the concept of the invention in more detail but are not intended to restrict the equivalence range of the invention.

REFERENCES

1. Clark, C. M., L. Sheppard, G. G. Fillenbaum, D. Galasko, J. C. Morris, E. Koss, R. Mohs, and A. Heyman. 1999. Variability in annual Mini-Mental State Examination score in patients with probable Alzheimer disease: a clinical perspective of data from the Consortium to Establish a Registry for Alzheimer's Disease. *Arch Neurol.* 56:857–62.

2. Ikeda, T., Y. Nagai, A. Yamaguchi, S. Yokose, and S. Yoshiki. 1995. Age-related reduction in bone matrix protein mRNA expression in rat bone tissues: application of histo-morphometry to in situ hybridization. *Bone.* 16:17–23.

3. McKee, M. D., A. Nanci, W. J. Landis, Y. Gotoh, L. C. Gerstenfeld, and M. J. Glimcher. 1990. Developmental appearance and ultrastructural immunolocalization of a major 66 kDa phosphoprotein in embryonic and post-natal chicken bone. *Anat Rec.* 228:77–92.

4. Weber, G. F., S. Ashkar, M. J. Glimcher, and H. Cantor. 1996. Receptor-ligand interaction between CD44 and osteopontin (Eta-1). *Science.* 271:509–12.

5. Weber, G. F., and H. Cantor. 1996. The immunology of Eta-1/osteopontin. *Cytokine Growth Factor Rev.* 7:241–8.

6. Gunnersen, J. M., V. Spirkoska, P. E. Smith, R. A. Danks, and S. S. Tan. 2000. Growth and migration markers of rat C6 glioma cells identified by serial analysis of gene expression. *Glia.* 32:146–54.

7. Sørensen, E. S., P. Hojrup, and T. E. Petersen. 1995. Posttranslational modifications of bovine osteopontin: identification of twenty-eight phosphorylation and three O-glycosylation sites. *Protein Sci.* 4:2040–9.

8. Nagata, T., R. Todescan, H. A. Goldberg, Q. Zhang, and J. Sodek. 1989. Sulphation of secreted phosphoprotein I (SPPI, osteopontin) is associated with mineralized tissue formation. *Biochem Biophys Res Commun.* 165:234–40.

9. Liang, C. T., J. Barnes, J. G. Seedor, H. A. Quartuccio, M. Bolander, J. J. Jeffrey, and G. A. Rodan. 1992. Impaired bone activity in aged rats: alterations at the cellular and molecular levels. *Bone.* 13:435–41.

10. Tanaka, H., R. Quarto, S. Williams, J. Barnes, and C. T. Liang. 1994. In vivo and in vitro effects of insulin-like growth factor-1 (IGF-1) on femoral mRNA expression in old rats. *Bone.* 15:647–53.

11. Kwon, H. M., B. K. Hong, T. S. Kang, K. Kwon, H. K. Kim, Y. Jang, D. Chol, H. Y. Park, S. M. Kang, S. Y. Cho, and H. S. Kim. 2000. Expression of osteopon tin in calcified coronary atherosclerotic plaques. *J Korean Med Sci.* 15:485–93.

12. Ek-Rylander, B., M. Flores, M. Wendel, D. Heinegard, and G. Andersson. 1994. Dephosphorylation of osteopontin and bone sialoprotein by osteoclastic tartrate-resistant acid phosphatase. Modulation of osteoclast adhesion in vitro. *J. Biol Chem.* 269:14853–6.

13. Hunter, G. K., C. L. Kyle, and H. A. Goldberg. 1994. Modulation of crystal formation by bone phospho-proteins: structural specificity of the osteopontin-mediated inhibition of hydroxyapatite formation. *Biochem J.* 300:723–8.

14. Wang, X., C. Louden, T. L. Yue, J. A. Ellison, F. C. Barone, H. A. Solleveld, and G. Z. Feuerstein. 1998. Delayed expression of osteopontin after focal stroke in the rat. *J Neurosci.* 18:2075–83.

15. Liaw, L., D. E. Birk, C. B. Ballas, J. S. Whitsitt, J. M. Davidson, and B. L. Hogan. 1998. Altered wound healing in mice lacking a functional osteopontin gene (sppl). *J Clin Invest.* 101:1468–78.

16. Ellison, J. A., J. J. Velier, P. Spera, Z. L. Jonak, X. Wang, F. C. Barone, and G. Z. Feuerstein. 1998. Osteopontin and its integrin receptor alpha(v)beta3 are upregulated during formation of the glial scar after focal stroke. *Stroke.* 29:1698–706; discussion 1707.

17. Wilm, M., and M. Mann. 1996. Analytical properties of the nanoelectrospray ion source. *Anal Chem.* 68:1–8.

18. Engelborghs, S., and P. P. De Deyn. 2001. Biological and genetic markers of sporadic Alzheimer's disease. *Acta Med Okayama.* 55:55–63.

19. Papayannopoulos, I. A. 1995. The interpretation of collision-induced dissociation tandem mass spectra of peptides. *Mass Spectrom Rev:* 49–73.

20. Perkins, D. N., D. J. Pappin, D. M. Creasy, and J. S. Cottrell. 1999. Probability-based protein identification by searching sequence databases using mass spectrometry data. *Electrophoresis.* 20:3551–67.

The invention claimed is:

1. A method for detecting Alzheimer's disease in a patient, comprising the step of identifying, in a biological sample from said patient, an elevated concentration of at least one dementia-related osteopontin marker peptide selected from the group consisting of DROPN-5(SEQ ID NO:5), DROPN-10(SEQ ID NO:10), DROPN-20(SEQ ID NO:20), and phosphorylated DROPN-10(SEQ ID NO:10), when compared to a control, said elevated concentration of said at least one dementia-related osteopontin marker peptide being indicative of the existence of Alzheimer's disease in said patient.

2. The method as claimed in claim 1, wherein the step of identifying includes the step of determining the relative concentration of said at least one marker peptide, compared with the concentration of the same peptide in a control sample, where
   a) the concentration change, which is specific for the particular marker peptide, in the biological sample is found relative to a control sample, and
   b) a significant marker peptide concentration change with an error probability of less than at least in 90% a) is regarded as positive detection result for the chronic dementia disease.

3. The method as claimed in claim 1, wherein the identifying step is carried out in combination with a mini-mental state examination or a mini-mental score to increase the sensitivity and/or specificity thereof.

4. The method as claimed in claim 1, wherein the at least one dementia related osteopontin marker peptide is in unmodified form, in chemically modified form or has post-translational modifications selected from the group consisting of phosphorylation and addition of an N-terminal pryoglutamic acid group.

5. The method as claimed in claims 1, wherein the biological sample is cerebrospinal fluid, serum, plasma, urine, synovial fluid, sputum, stool, tear fluid or a tissue homogenate.

6. The method as claimed in claim 1, wherein the step of identifying is carried out with the aid of a mass spectrometric determination, preferably a MALDI (matrix-assisted laser desorption and ionization) mass spectrometry.

7. The method as claimed in claim 6, wherein the step of identifying comprises the mass spectrometric determination of at least one of the theoretical, monoisotopic mass peaks of 2627.2715/≧1009.4716/4032.7594/4465.0079/ 3718.6368/1737.8030/1900.8664/≧956.4087/≧895.4148/ 7653.6003/4662.0953/2093.9304/≧899.3985/≧1087.4835/ 1522.7991/1635.8832/1763.9781/1911.0466/3222.6521/

3435.7634/1650.8941/1797.9625/3109.5680/2796.4042/≧1112.5826/≧844.3563/2526.2238/2528.2031 or of 3718.6368 dalton and/or one of the experimentally determined masses of 7738/7818/7898/7978 and 8058 dalton.

8. The method as claimed in claim 1, wherein the at least one dementia-related osteopontin marker peptide is identified with the aid of an immunological, physical or chemical test.

9. The method as claimed in claim 1, wherein the biological sample is fractionated chromatographically before the identification step using reverse phase chromatography or high resolution reverse phase chromatography.

10. The method as claimed in claim 1, wherein the biological sample is fractionated before the identification step by precipitation reactions or liquid phase separations.

* * * * *

SEQUENCE LISTING

<160> NUMBER OF SEQ ID NOS: 32

<210> SEQ ID NO 1
<211> LENGTH: 24
<212> TYPE: PRT
<213> ORGANISM: Homo sapiens

<400> SEQUENCE: 1

Val Lys Gln Ala Asn Ser Gly Ser Ser Glu Glu Lys Gln Leu Tyr Asn
1               5                   10                  15

Lys Tyr Pro Asp Ala Val Ala Thr
            20

<210> SEQ ID NO 2
<211> LENGTH: 8
<212> TYPE: PRT
<213> ORGANISM: Homo sapiens

<400> SEQUENCE: 2

Ser Glu Glu Lys Gln Leu Tyr Asn
1               5

<210> SEQ ID NO 3
<211> LENGTH: 36
<212> TYPE: PRT
<213> ORGANISM: Homo sapiens

```
<400> SEQUENCE: 3

Ala Gln Asp Leu Asn Ala Pro Ser Asp Trp Asp Ser Arg Gly Lys Asp
1               5                   10                  15

Ser Tyr Glu Thr Ser Gln Leu Asp Asp Gln Ser Ala Glu Thr His Ser
            20                  25                  30

His Lys Gln Ser
        35

<210> SEQ ID NO 4
<211> LENGTH: 39
<212> TYPE: PRT
<213> ORGANISM: Homo sapiens

<400> SEQUENCE: 4

Ala Gln Asp Leu Asn Ala Pro Ser Asp Trp Asp Ser Arg Gly Lys Asp
1               5                   10                  15

Ser Tyr Glu Thr Ser Gln Leu Asp Asp Gln Ser Ala Glu Thr His Ser
            20                  25                  30

His Lys Gln Ser Arg Leu Tyr
        35

<210> SEQ ID NO 5
<211> LENGTH: 33
<212> TYPE: PRT
<213> ORGANISM: Homo sapiens

<400> SEQUENCE: 5

Leu Asn Ala Pro Ser Asp Trp Asp Ser Arg Gly Lys Asp Ser Tyr Glu
1               5                   10                  15

Thr Ser Gln Leu Asp Asp Gln Ser Ala Glu Thr His Ser His Lys Gln
            20                  25                  30

Ser

<210> SEQ ID NO 6
<211> LENGTH: 15
<212> TYPE: PRT
<213> ORGANISM: Homo sapiens

<400> SEQUENCE: 6

Asp Asp Gln Ser Ala Glu Thr His Ser His Lys Gln Ser Arg Leu
1               5                   10                  15

<210> SEQ ID NO 7
<211> LENGTH: 16
<212> TYPE: PRT
<213> ORGANISM: Homo sapiens

<400> SEQUENCE: 7

Asp Asp Gln Ser Ala Glu Thr His Ser His Lys Gln Ser Arg Leu Tyr
1               5                   10                  15

<210> SEQ ID NO 8
<211> LENGTH: 8
<212> TYPE: PRT
<213> ORGANISM: Homo sapiens

<400> SEQUENCE: 8

Lys Asp Ser Tyr Glu Thr Ser Gln
1               5
```

<210> SEQ ID NO 9
<211> LENGTH: 8
<212> TYPE: PRT
<213> ORGANISM: Homo sapiens

<400> SEQUENCE: 9

Ser Ala Glu Thr His Ser His Lys
1               5

<210> SEQ ID NO 10
<211> LENGTH: 66
<212> TYPE: PRT
<213> ORGANISM: Homo sapiens

<400> SEQUENCE: 10

Lys Ala Asn Asp Glu Ser Asn Glu His Ser Asp Val Ile Asp Ser Gln
1               5                   10                  15

Glu Leu Ser Lys Val Ser Arg Glu Phe His Ser His Glu Phe His Ser
            20                  25                  30

His Glu Asp Met Leu Val Val Asp Pro Lys Ser Lys Glu Glu Asp Lys
        35                  40                  45

His Leu Lys Phe Arg Ile Ser His Glu Leu Asp Ser Ala Ser Ser Glu
    50                  55                  60

Val Asn
65

<210> SEQ ID NO 11
<211> LENGTH: 40
<212> TYPE: PRT
<213> ORGANISM: Homo sapiens

<400> SEQUENCE: 11

Lys Ala Asn Asp Glu Ser Asn Glu His Ser Asp Val Ile Asp Ser Gln
1               5                   10                  15

Glu Leu Ser Lys Val Ser Arg Glu Phe His Ser His Glu Phe His Ser
            20                  25                  30

His Glu Asp Met Leu Val Val Asp
        35                  40

<210> SEQ ID NO 12
<211> LENGTH: 17
<212> TYPE: PRT
<213> ORGANISM: Homo sapiens

<400> SEQUENCE: 12

Ser Lys Val Ser Arg Glu Phe His Ser His Glu Phe His Ser His Glu
1               5                   10                  15

Asp

<210> SEQ ID NO 13
<211> LENGTH: 8
<212> TYPE: PRT
<213> ORGANISM: Homo sapiens

<400> SEQUENCE: 13

Ser Asn Glu His Ser Asp Val Ile
1               5

<210> SEQ ID NO 14
<211> LENGTH: 8
<212> TYPE: PRT
<213> ORGANISM: Homo sapiens

```
<400> SEQUENCE: 14

Arg Glu Phe His Ser His Glu Phe
1               5

<210> SEQ ID NO 15
<211> LENGTH: 13
<212> TYPE: PRT
<213> ORGANISM: Homo sapiens

<400> SEQUENCE: 15

Leu Val Val Asp Pro Lys Ser Lys Glu Glu Asp Lys His
1               5                   10

<210> SEQ ID NO 16
<211> LENGTH: 14
<212> TYPE: PRT
<213> ORGANISM: Homo sapiens

<400> SEQUENCE: 16

Leu Val Val Asp Pro Lys Ser Lys Glu Glu Asp Lys His Leu
1               5                   10

<210> SEQ ID NO 17
<211> LENGTH: 15
<212> TYPE: PRT
<213> ORGANISM: Homo sapiens

<400> SEQUENCE: 17

Leu Val Val Asp Pro Lys Ser Lys Glu Glu Asp Lys His Leu Lys
1               5                   10                  15

<210> SEQ ID NO 18
<211> LENGTH: 16
<212> TYPE: PRT
<213> ORGANISM: Homo sapiens

<400> SEQUENCE: 18

Leu Val Val Asp Pro Lys Ser Lys Glu Glu Asp Lys His Leu Lys Phe
1               5                   10                  15

<210> SEQ ID NO 19
<211> LENGTH: 28
<212> TYPE: PRT
<213> ORGANISM: Homo sapiens

<400> SEQUENCE: 19

Leu Val Val Asp Pro Lys Ser Lys Glu Glu Asp Lys His Leu Lys Phe
1               5                   10                  15

Arg Ile Ser His Glu Leu Asp Ser Ala Ser Ser Glu
            20                  25

<210> SEQ ID NO 20
<211> LENGTH: 30
<212> TYPE: PRT
<213> ORGANISM: Homo sapiens

<400> SEQUENCE: 20

Leu Val Val Asp Pro Lys Ser Lys Glu Glu Asp Lys His Leu Lys Phe
1               5                   10                  15

Arg Ile Ser His Glu Leu Asp Ser Ala Ser Ser Glu Val Asn
            20                  25                  30
```

```
<210> SEQ ID NO 21
<211> LENGTH: 14
<212> TYPE: PRT
<213> ORGANISM: Homo sapiens

<400> SEQUENCE: 21

Val Val Asp Pro Lys Ser Lys Glu Glu Asp Lys His Leu Lys
1               5                   10

<210> SEQ ID NO 22
<211> LENGTH: 15
<212> TYPE: PRT
<213> ORGANISM: Homo sapiens

<400> SEQUENCE: 22

Val Val Asp Pro Lys Ser Lys Glu Glu Asp Lys His Leu Lys Phe
1               5                   10                  15

<210> SEQ ID NO 23
<211> LENGTH: 27
<212> TYPE: PRT
<213> ORGANISM: Homo sapiens

<400> SEQUENCE: 23

Val Val Asp Pro Lys Ser Lys Glu Glu Asp Lys His Leu Lys Phe Arg
1               5                   10                  15

Ile Ser His Glu Leu Asp Ser Ala Ser Ser Glu
            20                  25

<210> SEQ ID NO 24
<211> LENGTH: 24
<212> TYPE: PRT
<213> ORGANISM: Homo sapiens

<400> SEQUENCE: 24

Pro Lys Ser Lys Glu Glu Asp Lys His Leu Lys Phe Arg Ile Ser His
1               5                   10                  15

Glu Leu Asp Ser Ala Ser Ser Glu
            20

<210> SEQ ID NO 25
<211> LENGTH: 9
<212> TYPE: PRT
<213> ORGANISM: Homo sapiens

<400> SEQUENCE: 25

Lys Ser Lys Glu Glu Asp Lys His Leu
1               5

<210> SEQ ID NO 26
<211> LENGTH: 8
<212> TYPE: PRT
<213> ORGANISM: Homo sapiens

<400> SEQUENCE: 26

Ser His Glu Leu Asp Ser Ala Ser
1               5

<210> SEQ ID NO 27
<211> LENGTH: 23
<212> TYPE: PRT
<213> ORGANISM: Homo sapiens

<400> SEQUENCE: 27
```

Val Lys Gln Ala Asp Ser Gly Ser Ser Glu Glu Lys Gln Leu Tyr Asn
1               5                   10                  15

Lys Tyr Pro Asp Ala Val Ala
            20

<210> SEQ ID NO 28
<211> LENGTH: 23
<212> TYPE: PRT
<213> ORGANISM: Homo sapiens

<400> SEQUENCE: 28

Lys Gln Ala Asp Ser Gly Ser Ser Glu Glu Lys Gln Leu Tyr Asn Lys
1               5                   10                  15

Tyr Pro Asp Ala Val Ala Thr
            20

<210> SEQ ID NO 29
<211> LENGTH: 33
<212> TYPE: PRT
<213> ORGANISM: Homo sapiens

<400> SEQUENCE: 29

Leu Asn Ala Pro Ser Asp Trp Asp Ser Arg Gly Lys Asp Ser Tyr Glu
1               5                   10                  15

Thr Ser Gln Leu Asp Asp Gln Ser Ala Glu Thr His Ser His Lys Gln
            20                  25                  30

Ser

<210> SEQ ID NO 30
<211> LENGTH: 35
<212> TYPE: PRT
<213> ORGANISM: Homo sapiens

<400> SEQUENCE: 30

Asn Asp Glu Ser Asn Glu His Ser Asp Val Ile Asp Ser Gln Glu Leu
1               5                   10                  15

Ser Lys Val Ser Arg Glu Phe His Ser His Glu Phe His Ser His Glu
            20                  25                  30

Asp Met Leu
        35

<210> SEQ ID NO 31
<211> LENGTH: 34
<212> TYPE: PRT
<213> ORGANISM: Homo sapiens

<400> SEQUENCE: 31

Asn Asp Glu Ser Asn Glu His Ser Asp Val Ile Asp Ser Gln Glu Leu
1               5                   10                  15

Ser Lys Val Ser Arg Glu Phe His Ser His Glu Phe His Ser His Glu
            20                  25                  30

Asp Met

<210> SEQ ID NO 32
<211> LENGTH: 1424
<212> TYPE: DNA
<213> ORGANISM: Homo sapiens

<400> SEQUENCE: 32
gaccagactc gtctcaggcc agttgcagcc ttctcagcca aacgccgacc aaggaaaact      60

-continued

```
cactaccatg agaattgcag tgatttgctt ttgcctccta ggcatcacct gtgccatacc    120
agttaaacag gctgattctg gaagttctga ggaaaagcag ctttacaaca aatacccaga    180
tgctgtggcc acatggctaa accctgaccc atctcagaag cagaatctcc tagcccaca     240 gaatgctgtg tcctctgaag aaaccaatga ctttaaacaa gagacccttc caagtaagtc    300
caacgaaagc catgaccaca tggatgatat ggatgatgaa gatgatgatg accatgtgga    360
cagccaggac tccattgact cgaacgactc tgatgatgta gatgacactg atgattctca    420
ccagtctgat gagtctcacc attctgatga atctgatgaa ctggtcactg attttcccac    480
ggacctgcca gcaaccgaag ttttcactcc agttgtcccc acagtagaca catatgatgg    540
ccgaggtgat agtgtggttt atggactgag gtcaaaatct aagaagtttc gcagacctga    600
catccagtac cctgatgcta cagacgagga catcacctca cacatggaaa gcgaggagtt    660
gaatggtgca tacaaggcca tccccgttgc ccaggacctg aacgcgcctt ctgattggga    720
cagccgtggg aaggacagtt atgaaacgag tcagctggat gaccagagtg ctgaaaccca    780
cagccacaag cagtccagat tatataagcg gaaagccaat gatgagagca atgagcattc    840
cgatgtgatt gatagtcagg aactttccaa agtcagccgt gaattccaca gccatgaatt    900
tcacagccat gaagatatgc tggttgtaga ccccaaaagt aaggaagaag ataaacacct    960
gaaatttcgt atttctcatg aattagatag tgcatcttct gaggtcaatt aaaaggagaa   1020
aaaatacaat ttctcacttt gcatttagtc aaaagaaaaa atgctttata gcaaaatgaa   1080
agagaacatg aaatgcttct ttctcagttt attggttgaa tgtgtatcta tttgagtctg   1140
gaaataacta atgtgtttga taattagttt agtttgtggc ttcatggaaa ctccctgtaa   1200
actaaaagct tcagggttat gtctatgttc attctataga agaaatgcaa actatcactg   1260
tattttaata tttgttattc tctcatgaat agaaatttat gtagaagcaa acaaaatact   1320
tttacccact taaaaagaga atataacatt ttatgtcact ataatctttt gttttttaag   1380
ttagtgtata ttttgttgtg attatctttt tgtggtgtga ataa                    1424
```